US012557997B2

(12) United States Patent　　　　　　(10) Patent No.:　　US 12,557,997 B2
Quan et al.　　　　　　　　　　　　　(45) Date of Patent:　　Feb. 24, 2026

(54) PROXIMITY SENSOR CIRCUITS AND RELATED SENSING METHODS

(71) Applicant: The Board of Trustees of the Leland Stanford Junior University, Stanford, CA (US)

(72) Inventors: Xina Quan, Saratoga, CA (US); Zhenan Bao, Stanford, CA (US); Amanda Nguyen, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 729 days.

(21) Appl. No.: 16/088,700

(22) PCT Filed: Mar. 29, 2017

(86) PCT No.: PCT/US2017/024838
§ 371 (c)(1),
(2) Date: Sep. 26, 2018

(87) PCT Pub. No.: WO2017/172978
PCT Pub. Date: Oct. 5, 2017

(65) Prior Publication Data
US 2020/0305740 A1　　Oct. 1, 2020

Related U.S. Application Data

(60) Provisional application No. 62/314,474, filed on Mar. 29, 2016.

(51) Int. Cl.
*A61B 5/024*　　　(2006.01)
*A61B 5/00*　　　(2006.01)
(Continued)

(52) U.S. Cl.
CPC ...... *A61B 5/02444* (2013.01); *A61B 5/02007* (2013.01); *A61B 5/02108* (2013.01);
(Continued)

(58) Field of Classification Search
None
See application file for complete search history.

(56) References Cited

U.S. PATENT DOCUMENTS 3,545,430 A * 12/1970 Stepan ................. A61B 5/0535
　　　　　　　　　　　　　　　　　　600/507
3,742,937 A　　7/1973 Manuel et al.
(Continued)

FOREIGN PATENT DOCUMENTS

CN　　　101330868 A　　12/2008
CN　　　101484070 A　　7/2009
(Continued)

OTHER PUBLICATIONS

"Definition of CONFORM." Dictionary.Com, Mar. 18, 2016, www. dictionary.com/browse/conform (Year: 2016).*
(Continued)

*Primary Examiner* — Jacqueline Cheng
*Assistant Examiner* — Jairo H Portillo
(74) *Attorney, Agent, or Firm* — Crawford Maunu PLLC

(57) ABSTRACT

Various embodiments include an apparatus and methods of use of a proximity sensor. An example apparatus includes a transducer circuit having a sensor circuit, the sensor circuit including an electrode, an electrical-signal sensing circuit, a substrate to support and at least partially enclose the transducer circuit and the electrical-signal sensing circuit, and a communication circuit. The transducer circuit converts changes in capacitance into electrical signals, the changes in capacitance being carried by the electrode and being responsive to pressure and/or electric field modulations attributable
(Continued)

to hemodynamic or pulse-wave events. The electrical-signal sensing circuit senses the events in response to the electrical signals from the transducer circuit. The substrate can conform to a portion of a user and locate the sensor circuit sufficiently close to the user's skin for electrically sensing the hemodynamic or pulse-wave events. The communication circuit responds to the electrical-signal sensing circuit by sending data indicative of the hemodynamic monitoring.

21 Claims, 24 Drawing Sheets

(51) Int. Cl.
      *A61B 5/02*         (2006.01)
      *A61B 5/021*        (2006.01)
(52) U.S. Cl.
      CPC .......... *A61B 5/02438* (2013.01); *A61B 5/681*
                    (2013.01); *A61B 5/6844* (2013.01)

(56)                    References Cited

U.S. PATENT DOCUMENTS

| | | | | | |
|---|---|---|---|---|---|
| 5,179,956 | A | * | 1/1993 | Harada | A61B 5/02233 |
| | | | | | 73/756 |
| 5,325,728 | A | * | 7/1994 | Zimmerman | A61B 5/0265 |
| | | | | | 73/861.12 |
| 5,608,417 | A | | 3/1997 | de Vall | |
| 6,017,313 | A | | 1/2000 | Bratteli et al. | |
| 6,491,647 | B1 | * | 12/2002 | Bridger | G01L 1/2231 |
| | | | | | 128/900 |
| 6,941,647 | B2 | | 9/2005 | Cho et al. | |
| 7,052,469 | B2 | | 5/2006 | Minamiura et al. | |
| 7,147,604 | B1 | | 12/2006 | Allen et al. | |
| 7,935,061 | B1 | * | 5/2011 | Breed | A61B 5/021 |
| | | | | | 600/485 |
| 8,847,844 | B2 | | 9/2014 | Kato et al. | |
| 10,495,713 | B2 | | 12/2019 | Hsiao et al. | |
| 2002/0143260 | A1 | * | 10/2002 | Ogura | A61B 5/022 |
| | | | | | 600/500 |
| 2004/0073104 | A1 | | 4/2004 | Brun del Re et al. | |
| 2004/0267165 | A1 | * | 12/2004 | Sarvazyan | A61B 5/0002 |
| | | | | | 600/587 |
| 2006/0056161 | A1 | | 3/2006 | Shin et al. | |
| 2007/0100666 | A1 | * | 5/2007 | Stivoric | G05B 1/01 |
| | | | | | 374/E1.002 |
| 2007/0282227 | A1 | * | 12/2007 | Nanba | A61B 5/6838 |
| | | | | | 600/595 |
| 2008/0211519 | A1 | * | 9/2008 | Kurumado | G01D 5/24 |
| | | | | | 324/688 |
| 2008/0262364 | A1 | | 10/2008 | Aarts | |
| 2010/0106027 | A1 | * | 4/2010 | Jaeger | A61B 5/1135 |
| | | | | | 600/484 |
| 2010/0148804 | A1 | | 6/2010 | Jakoby et al. | |
| 2010/0309167 | A1 | * | 12/2010 | Nam | G06F 3/0443 |
| | | | | | 345/174 |
| 2010/0324498 | A1 | | 12/2010 | Christiansen | |
| 2011/0050647 | A1 | * | 3/2011 | Lee | G06F 3/042 |
| | | | | | 345/175 |
| 2011/0137200 | A1 | * | 6/2011 | Yin | A61B 5/7214 |
| | | | | | 600/547 |
| 2011/0224529 | A1 | * | 9/2011 | Lading | A61B 5/02007 |
| | | | | | 600/384 |
| 2011/0248729 | A2 | | 10/2011 | Mueller et al. | |
| 2012/0062245 | A1 | * | 3/2012 | Bao | H01L 29/84 |
| | | | | | 324/661 |
| 2012/0175714 | A1 | * | 7/2012 | Lakamraju | G06F 3/0412 |
| | | | | | 257/E27.006 |
| 2013/0041244 | A1 | * | 2/2013 | Woias | A61B 5/0215 |
| | | | | | 600/381 |
| 2014/0071082 | A1 | * | 3/2014 | Singh | G06F 3/04182 |
| | | | | | 345/174 |
| 2014/0081160 | A1 | * | 3/2014 | Xiang | A61B 5/02444 |
| | | | | | 29/622 |
| 2014/0081175 | A1 | * | 3/2014 | Telfort | A61B 7/04 |
| | | | | | 600/586 |
| 2015/0051468 | A1 | | 2/2015 | Srinivasa et al. | |
| 2015/0157269 | A1 | | 6/2015 | Lisogurski et al. | |
| 2015/0161783 | A1 | * | 6/2015 | Chang | G06T 7/0012 |
| | | | | | 382/116 |
| 2015/0216406 | A1 | * | 8/2015 | Furukawa | A61B 3/0041 |
| | | | | | 600/558 |
| 2015/0230863 | A1 | * | 8/2015 | Youngquist | A61B 5/4833 |
| | | | | | 606/9 |
| 2015/0272455 | A1 | | 10/2015 | Krasnov et al. | |
| 2015/0327784 | A1 | | 11/2015 | Lading et al. | |
| 2016/0033343 | A1 | | 2/2016 | Park et al. | |
| 2016/0051195 | A1 | | 2/2016 | Pang et al. | |
| 2016/0143587 | A1 | * | 5/2016 | White | A61B 5/6844 |
| | | | | | 600/300 |
| 2016/0246396 | A1 | * | 8/2016 | Dickinson | G06F 3/043 |
| 2016/0310034 | A1 | * | 10/2016 | Tonar | A61B 5/4875 |
| 2017/0020402 | A1 | | 1/2017 | Rogers et al. | |
| 2020/0352455 | A1 | | 11/2020 | Banet et al. | |

FOREIGN PATENT DOCUMENTS

| | | | |
|---|---|---|---|
| CN | 101584581 | A | 11/2009 |
| CN | 103354729 | A | 10/2013 |
| CN | 103781416 | A | 5/2014 |
| CN | 204428023 | U | 7/2015 |
| CN | 106413528 | A | 2/2017 |
| EP | 2668896 | A1 | 12/2012 |
| EP | 2578141 | A1 | 4/2013 |
| JP | 2005021452 | A | 1/2005 |
| JP | 2009066356 | A | 4/2009 |
| JP | 2013534833 | A | 9/2013 |
| WO | 2008011592 | A2 | 1/2008 |
| WO | 2008/122806 | A1 | 10/2008 |
| WO | 2012155157 | A1 | 11/2012 |

OTHER PUBLICATIONS

Cecelja, M. et al. "Role of Arterial Stiffness in Cardiovascular Disease." JRSM Cardiovascular Disease 1.4 (2012): 10 pages.
Donley, D. A. et al. "Aerobic exercise training reduces arterial stiffness in metabolic syndrome" Journal of Applied Physiology, vol. 116, No. 11 (Jun. 2014): 1396-1404.
Baruch, M. C., et al. "Validation of the pulse decomposition analysis algorithm using central arterial blood pressure." Biomedical Engineering Online 13.96 (2014): 19 pages.
Munir, S. et al. "Peripheral augmentation index defines the relationship between central and peripheral pulse pressure." Hypertension 51.1 (2008): 112-118.
Lee, Byoung-Kwon. "Computational fluid dynamics in cardiovascular disease." Korean circulation journal 41.8 (2011): 423-430.
Xiaoman, Xing et al. "Optical blood pressure estimation with photoplethysmography and FFT-based neural networks," Biomed. Opt. Express 7, (2016): 3007-3020.
Malmivuo, J et al. "Chapter 25: Impedance Plethysmography." Bioelectromagnetism—Principles and Applications of Bioelectric and Biomagnetic Fields, Oxford University Press (1995): 22 pages.
Yamamoto, Y. et al. (1991): Impedance plethysmography in human limbs. Part 1. On electrodes and electrode geometry. Med. & Biol. Eng. & Comput. 29: 419-24. Abstract Only.
USPTO. International Search Report & Opinion for related PCT Application No. PCT/US2017/024838 mailed on Jun. 22, 2017, 9 pages.
EPO. Supplementary European Search Report and Opinion dated Oct. 17, 2019, for counterpart European Patent Application No. 17776588.0 (9 pages).
L. Lading et al. "Sensor for vascular compliance and blood pressure." IEEE SENSORS 2009 Conference, pp. 181-184.
CIPO. Office Action and Search Report dated Dec. 2, 2020, for counterpart Chinese Patent Application No. 201780022422.0 (5 pages).

(56) References Cited

OTHER PUBLICATIONS

JPO. Office Action dated Feb. 9, 2021, for counterpart Japanese Patent Application No. 2018-551788 (6 pages).

CIPO. Office Action dated Aug. 9, 2021 (with appended translation), for counterpart Chinese Patent Application No. 201780022422.0. The Examiner is respectfully referred to Applicant's IDS filed Nov. 15, 2019, for any reference cited in the foreign office action.

JPO. Office Action dated Sep. 7, 2021 (with appended machine translation), for counterpart Japanese Patent Application No. 2018-551788. The Examiner is respectfully referred to Applicant's IDS filed Mar. 12, 2021, for any reference cited in the foreign office action.

CIPO. Office Action dated Jul. 11, 2022, with English translation, for counterpart Chinese Patent Application No. 201780022422.0 (33 pgs). The Examiner is referred again to this copending prosecution, and Applicant's IDSs filed Nov. 15, 2019 and Mar. 11, 2022, which listed the D1 (WO '157) and D2 (US '468) references cited in the Chinese Office Action.

CIPO. Office Action dated Mar. 10, 2022, for counterpart Chinese Patent Application No. 201780022422.0. The Examiner is respectfully referred to this copending prosecution, and Applicant's IDS filed Nov. 15, 2019, for the WO '157 (D1) reference cited in the foreign office action.

Elgendi M. On the analysis of fingertip photoplethysmogram signals. Curr Cardiol Rev. Feb. 2012;8(1):14-25.

JPO. Office Action dated Nov. 21, 2023, with English machine translation, for counterpart Japanese Divisional Patent Application No. 2023-003741 (22 pgs). The Examiner is referred to this copending prosecution. Applicant also refers to the USPTO record for the instant Application (U.S. Appl. No. 16/088,700) in which the Examiner has previously cited and/or considered each of the listed references in the Japanese Office Action: D1 (US 20150051468A1). D2 (US 20160051195A1); and D3 (JP2005021452A, see Applicant's IDS filed Mar. 12, 2021).

USPTO. Final Office Action dated Oct. 15, 2024, for U.S. Appl. No. 17/287,805. The Examiner is respectfully referred to this copending patent prosecution of the common Applicant/Assignee.

CIPO. Office Action dated Mar. 19, 2025, with English-machine translation, for counterpart Chinese Patent Application No. 202310114035.7 (11 pgs). The Examiner is referred to this copending foreign prosecution, and to Applicant's IDSs filed Nov. 15, 2019, Mar. 11, 2022, and Aug. 10, 2022. In these IDSs, Applicant had provided to the Examiner, several patent references listed in this Chinese Office Action, as follows: US '269; WO '157; and US '468 references.

* cited by examiner

Data point index

Unfiltered data

1561

Filtered data

1562

Data point index

1559

PROXIMITY SENSOR CIRCUITS AND RELATED SENSING METHODS

OVERVIEW

Aspects of various embodiments are directed to proximity sensors and related sensing methods for sensing hemodynamic changes (or pulse-waveforms) of a user.

In the following discussion, various implementations and applications are disclosed to provide an understanding of the instant disclosure by way of non-limiting example embodiments.

In certain example embodiments, aspects of the present disclosure involve one or more sensor circuits configured and arranged to sense hemodynamic changes (or pulse-waveforms) of a user with the sensor circuit configured in a manner to monitor the physiologic changes of the user by using a single electrode placed near/onto a surface to be measured. These and other aspects employ the sensor circuit configured to sense the hemodynamic changes consistent with one more of the below-described embodiments and/or mechanisms.

More specific example embodiments are directed to an apparatus having at least one sensor circuit, the sensor circuit including an electrode, and an electrical-signal sensing circuit. The apparatus can be used to monitor one or more of the hemodynamic parameters in a non-invasive manner and in real-time. For example, the electrical-signal sensing circuit can sense pulse-wave events, while the sensor circuit is placed near or onto skin, by monitoring capacitance changes. The capacitance changes carried by the electrode are responsive to pressure and/or electric field modulations attributable to the pulse-wave events or to the changes in pressure or blood flow in the blood vessels (e.g., hemodynamics). The electrode can be used to determine capacitance changes between the electrode and the skin of the user. The sensor circuit including the electrode can be arranged with a transducer circuit, which is used to provide an electrical signal to the electrical-signal sensing circuit indicative of the changes in capacitance and/or pressure. Due to pulse-wave events, the distance between the skin of the user and the electrode can change and/or the electric field distribution around the blood vessels can change, resulting in a relative change in capacitance as measured using the sensor circuit. The changes in capacitance over time can be processed by the electrical-signal sensing circuit and used to generate and/or determine a pulse-waveform. In various embodiments, the pulse-waveform is correlated with various hemodynamic parameters. As specific examples, the pulse-waveform can be processed to determine a heart rate, blood pressure, arterial stiffness, and/or blood volume.

The electrode can be in contact with the skin of the user and/or in proximity. In some aspects, the electrode is constrained onto (whether in contact or not) the user using a mechanical constraint (e.g., a wristband, an elastically compliant band, or an article of clothing) and/or an adhesive. The electrode can be located near a blood vessel, preferably near a palpable pulse point such as but not limited to the radial, brachial, carotid, tibial, and temporal pulse points.

In other specific aspects, the apparatus includes a plurality of electrodes. For example, the apparatus can include a plurality of sensor circuits and each sensor circuit includes one of the plurality of electrodes. The plurality of electrodes can be arranged as part of a transducer circuit, which is used to provide electrical signals (e.g., a digital) to the electrical-signal sensing circuit indicative of the changes in capacitance that are responsive to modulations in distance between the skin of the user and the electrode, pressure and/or electric field and attributable to hemodynamic or pulse-wave events. In various related aspects, the plurality of sensor circuits are mechanically separated and/or arranged in an array (e.g., a sensor array). Each of the sensor circuits can be constructed differently, such as having different geometries, dielectric layers, locations, sensitivities, among other constructions as further described herein.

Various aspects are directed to a method of using the above-described apparatus. The method can include placing at least one electrode of an apparatus near or onto the skin of the user and sensing pulse-wave events. The pulse-wave events can be sensed while the at least one electrode is placed near or onto the skin of a user, using an electrical-signal sensing circuit of the apparatus, by monitoring capacitance changes that are responsive to pressure and/or electric field modulations attributable to hemodynamic or pulse-wave events. The pulse-wave events can be used to generate a pulse-waveform and/or to determine various hemodynamic parameters. For example, the method can include determining diastolic blood pressure, systolic blood pressure, arterial stiffness, and/or blood volume using the pulse-wave events.

A specific method can include use of flexible or bendable substrate of a wearable apparatus to secure the transducer circuit having at least one sensor circuit. The substrate supports and at least partially enclosing the transducer circuit and the electrical-signal sensing circuit. The substrate further conforms to a portion of a user including blood vessels and locates the at least one electrode sufficiently close to the user's skin for electrically sensing hemodynamic or pulse-wave events via the capacitance changes, the changes in capacitance being responsive to pressure and/or electric field modulations attributable to hemodynamic or pulse-wave events. A transducer circuit converts the changes in capacitance into the electrical signals. The method further includes sensing the hemodynamic or pulse-wave events in response to the electrical signals from the transducer circuit via the electrical-signal sensing circuit and using a communication circuit, within or outside the wearable apparatus, to respond to the electrical-signal sensing circuit by sending hemodynamic-monitoring data to an external circuit.

Other aspects are directed to an apparatus for use as part of a wearable device characterized by a flexible or bendable substrate configured and arranged to support and at least partially enclose a transducer circuit and an electrical-signal sensing circuit and to conform to a portion of a user including blood vessels for hemodynamic monitoring. The apparatus includes the transducer circuit having at least one sensor circuit, the sensor circuit including an electrode, the electrical-signal sensing circuit, and a communication circuit, as previously described above.

The above discussion/summary is not intended to describe each embodiment or every implementation of the present disclosure. The figures and detailed description that follow also exemplify various embodiments.

BRIEF DESCRIPTION OF FIGURES

Various example embodiments may be more completely understood in consideration of the following detailed description in connection with the accompanying drawings, in which:

FIGS. 4A-5B illustrate various example apparatus, in accordance with the present disclosure;

Figures 1A, 1B:
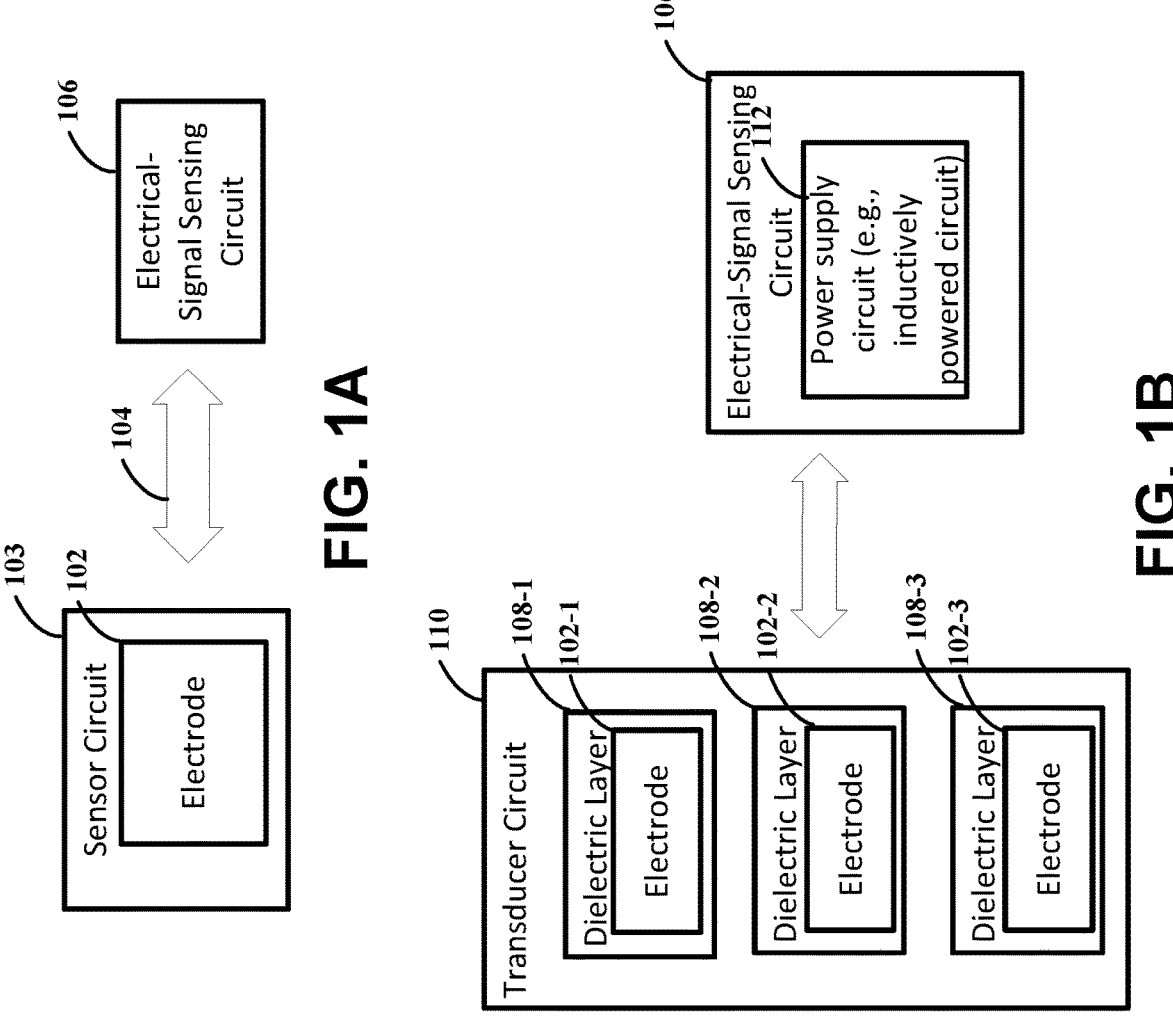
FIGS. 1A-1B show examples of apparatuses, in accordance with the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses including, and methods involving use of, a user-worn sensor circuit configured and arranged to sense pulse wave events aspects, conditions and/or attributes of the user. In certain implementations, aspects of the present disclosure have been shown to be beneficial when used in the context of a wrist-located or wrist-worn strap but it will be appreciated that the instant disclosure is not necessarily so limited. Various aspects may be appreciated through the following discussion of non-limiting examples which use exemplary contexts.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

Various embodiments of the present disclosure are directed toward an apparatus including at least one sensor circuit having an electrode and an electrical-signal sensing circuit. The apparatus can be used to monitor one or more hemodynamic parameters and pulse-wave events in a non-invasive manner and in real-time. Surprisingly, it has been discovered that a common floating ground and single electrode that does not need to touch a user's skin can be used for measuring pulse-wave events. In various embodiments, pulse-wave events can be monitored in a hands-free manner and without interference from environmental noise (e.g., human voices and other background noise, electrical interference and ambient light). The electrode (or array of electrodes) can consume relatively low amounts of power (e.g., between 5 microwatts and 3 milliwatts, although embodiments are not so limited). In some specific embodiments, the power consumption can be further reduced by only saving data after a trigger event (e.g., heart rate above a threshold, a particular heart event occurs such as an event indicative of a problem) and/or transmitting saved data in burst transmissions. The electrical-signal sensing circuit can sense pulse-wave events, while the at least one electrode is placed near or onto skin, by monitoring pressure differentials attributable to the pulse-wave events or capacitance changes attributable to the pulse-wave events. The electrode can be used to determine capacitance changes between the electrode and the skin of the user. Due to pulse-wave events, the distance between the skin of the user and the electrode can change, resulting in a relative change in capacitance and/or signal amplitude and quality as measured by the transducer circuit and the electrical-signal sensing circuit. The changes in capacitance over time can be processed by the electrical-signal sensing circuit and used to generate and/or determine a pulse-waveform. In various embodiments, the pulse-waveform is correlated with various hemodynamic parameters. As specific examples, the pulse-waveform can be processed to determine a heart rate, blood pressure, arterial stiffness, and/or blood volume. The electrode can be in contact with the skin of the user and/or in proximity. In some examples, the electrode can be sufficiently close to the user's skin for electrically sensing the hemodynamic or pulse-wave events via the capacitance changes carried by the electrode (or plurality of electrodes). In such examples, "sufficiently close" corresponds to a proximal distance, relative to the portion including the blood vessels, in a range from the furthest distance being 1 millimeter (mm) away from the skin and the nearest distance being zero, or in contact with the skin. In some aspects, the sensor circuit (e.g., the electrode) is constrained onto (whether in contact or not) the user using a mechanical constraint (e.g., flexible or bendable substrate, such as a wristband, sock, glove, sleeve, or other piece of wearable device or clothing) and/or an adhesive.

The changes in capacitance carried by the electrode and respective sensor circuit are responsive to pressure and/or electric field modulations attributable to hemodynamic or pulse-wave events. More specifically, the sensor circuit and electrode can capture (or sense) the capacitance changes through proximity sensing of the skin of the user (as opposed to physically deforming the device as a traditional capacitance sensor), and thereby act as or is a proximity sensor. The proximity sensing and/or capacitance changes are responsive to modulating distances between the skin of the user and the sensor circuit and/or modulating fringe field lines.

In other specific embodiments, the apparatus includes a plurality of electrodes. The plurality of electrodes can be arranged as part of a transducer circuit, which is used to provide a signal to the electrical-signal sensing circuit indicative of the changes in capacitance and/or pressure. For example, the transducer circuit can have a plurality of sensor circuits and each of the sensor circuits includes one of the plurality of electrodes. The electrical-signal sensing circuit can be arranged with the transducer circuit to monitor pressure differentials less than 1 kPa, such as in a range between 0.3 kilopascal (kPa) to 1 kPa. The different electrodes can have different geometries, sensitivities and/or be at different locations. The transducer circuit can convert changes in capacitance into electrical signals (e.g., digital signals). As described herein, the transducer circuit and the electrical-signal sensing circuit can be supported by and at least partially enclosed by the substrate.

Certain embodiments of the present disclosure are directed toward a method of using an apparatus, as previously described. The method can include placing at least one electrode of an apparatus near or onto the skin of the user and sensing pulse-wave events. The pulse-wave events can be sensed while the at least one electrode is placed near or onto the skin of a user, using an electrical-signal sensing circuit of the apparatus, by monitoring pressure differentials attributable to the pulse-wave events and/or monitoring capacitance changes (or relative capacitance changes) attributable to the pulse-wave events. The pulse-wave events can be used to generate a pulse-waveform and/or to determine various physiological and/or hemodynamic parameters. For example, the method can include determining diastolic blood pressure, systolic blood pressure, arterial stiffness, and/or blood volume using the pulse-wave events.

Somewhat surprisingly, pulse-wave events can be monitored using one or more electrodes placed on or near an arterial pulse point. For example, responsive to a pulse-wave event, each electrode can provide a signal indicative of the pulse-wave event. The electrode (or plurality of electrodes) is connected to circuitry, such as a transducer circuit. More specifically, each electrode (e.g., an electrical conductor) is connected to a respective sensor circuit which is used to measures or detects the signal indicative of the pulse-wave event (e.g., capacitance value and/or changes in capacitance) from the electrode and provides the signal to the transducer circuit. The transducer circuit than converts the signal indicative of the pulse-wave event to an electrical signal, which is provided to the electrical-signal sensing circuit. A pulse-wave event includes or refers to hemodynamic responses and/or attributes caused by and/or indicative of heart beats (e.g., contraction of heart muscles) (e.g., heart beats or sounds, pulsing of blood, etc.). The electrical-signal sensing circuit (and/or the transducer circuit) can include a commercially available or custom-designed circuit for capacitive touch screens and can be in wireless or wired communication with a central processing circuit (CPU). Further, the transducer circuit and/or the sensor circuit can have a floating ground. The signals measured using the electrode can be due to small pressure differences and/or surface displacements of the skin that modulate the fringe field at the electrode and resulting in measurable capacitance changes. The electrode(s) can be attached to the skin of a user (or other animal or being) using an adhesive (e.g., tape) or mechanically using a strap, such as a watchband, bracelet or wristband.

In specific embodiments, the electrode(s) is encapsulated with a dielectric layer (e.g., an encapsulant). When a plurality of electrodes are used, the dielectric layer on each of the plurality of electrodes can have different structural characteristics to modulate signal sensitivity of each electrode. Example characteristics can include thickness of the dielectric layer, composition of the dielectric material used, structures, and resistivity values, among other characteristics. Each of the plurality of electrodes can be associated with different characteristics based on at least one of electrode geometry and dielectric layers used with the electrode. The different electrodes can be used to output signals, responsive to monitored pulse-wave events. Signals from different electrodes can be used in a differential mode to eliminate signals that may be common to the electrodes, such as temperature changes and user motion (e.g., noise), and to enhance signals or pulse-wave events which may be measured by the more sensitive electrodes, such as pulse-waveform pressure differentials. In related specific embodiments, one or more of electrodes of the plurality of electrodes can be electrically shielded or isolated from one another. Further, spacers can be used to control or set the distance between at least one of the sensor circuits and/or electrodes and the skin of the user.

The signals provided by the electrode(s) can be used to determine various hemodynamic parameters. For example, responsive to a pulse-wave event, one or more signals indicative of capacitance changes are provided to the electrical-signal sensing circuit. As previously described, the capacitance changes, which are carried by at least one electrode, are responsive to pressure and/or electric field modulations attributable to hemodynamic or pulse-wave events. The electrical-signal sensing circuit uses the one or more signals to determine a heart rate, diastolic blood pressure, systolic blood pressure, and/or arterial stiffness. The signals can be processed using one or more bandpass filters or other signal processing techniques. For example, the signal can be filtered either digitally or through a circuit design used to minimize artifacts due to factors such as pressure changes or motion due to breathing, arm motions, and external vibrations.

These surprising findings can be particularly useful for monitoring blood pressure or other hemodynamic parameters in a non-invasive and/or continuous manner. In specific implementations, an apparatus can be used for providing sensitivity for pressure differentials and/or capacitance changes caused by pulse-wave events. Further, the apparatus and/or portions of the apparatus (e.g., the electrode) can be fabricated more easily than capacitive sensors as they have fewer design elements and material, making the end apparatus more robust.

In related-specific implementations, the apparatus includes or is a portion of a portable/wearable device and/or apparatus that can continuously monitor heart rate and other hemodynamic effects such diastolic blood pressure, systolic blood pressure, and arterial stiffness. As an example, a smart bandage can be applied over an arterial pulse point and can transmit data in real time to a receiver. Another example includes a smart watch band that provides a real-time read-out, stores and/or transmits the data. Other implementations are directed to small surface displacements or pressure differentials that can modulate the fringe fields at the electrode.

Turning now to the figures, FIGS. 1A-1B show examples of apparatuses, in accordance with the present disclosure. As illustrated by FIGS. 1A-1B, each apparatus includes a sensor circuit having an electrode and an electrical-signal sensing circuit. The apparatuses can monitor pressure differences and/or capacitance changes attributable to pulse-wave events and use the monitored pressure differences and/or capacitance changes to determine one or more hemodynamic parameters. The pulse-wave events can be used to generate waveforms or parts of the waveforms responsive to or indicative of a pulse of a user or animal (e.g., represents a tactile palpation of the heartbeat). The pulse-wave event can be captured as a signal and used to determine the hemodynamic parameter, such as a heart rate, diastolic blood pressure, systolic blood pressure, and/or arterial stiffness.

FIG. 1A illustrates an example apparatus comprising a sensor circuit 103 which includes an electrode 102, and an electrical-signal sensing circuit 106. The electrode 102 can be placed near or onto the skin of a user (or another animal). The electrical-signal sensing circuit 106 can include a proximity electrical-signal sensing circuit that senses pulse-wave events while the electrode 102 is placed near the skin or onto the skin of the user. In some embodiments, as further illustrated herein, the electrode 102 can be in direct contact with the skin or can be electrically or mechanically isolated from the skin, such as by air or dielectric material. The electrode 102 is used to sense pressure and/or capacitance changes that are attributable to pulse-wave events and output a signal indicative of the sensed pressure or capacitance changes to the electrical-signal sensing circuit 106 via the sensor circuit 103 and a communication path 104 (e.g., the electrode is connected to or plugged-in to the sensor circuit 103 which captures and outputs the signal indicative of a capacitance value). The electrical-signal sensing circuit 106 monitors the changes in pressure or capacitance (or relative capacitance changes) attributable to the pulse-wave events and determines a hemodynamic parameter, such as a heart-rate, from the same. The changes in pressure and/or capacitance can be measured based on relative changes in capacitance which may be caused by changes in distances between the electrode 102 and the skin of the user and/or changes in the electric fields around the blood vessels.

The sensor circuit 103 and/or the electrode 102 (or plurality of electrodes), in specific embodiments, are mechanically constrained to the skin or other body portion, such as by a wristband or a piece of clothing. The mechanical constraint can be via an elastic, flexible or bendable band and/or an adhesive that attaches the sensor circuit 103 and/or electrode 102 to the skin or body. The adhesive can be applied to the perimeter of the sensor circuit 103 (and not necessarily between the electrode 102 and the skin or other body portion). In other embodiments, the electrode 102 does not physically touch the skin, such as via spacers or otherwise, as described further herein. The capacitance changes of interest can be relative and not absolute values. The base capacitance of the electrode 102 can depend on the respective geometry and range of electrode 102 and/or the sensor circuit 103 design. In an example experimental embodiment, the electrical-signal sensing circuit 106 can measure an input range (e.g., capacitance changes) of plus and minus 15 picofarad (pF) with a maximum offset of 100 pF. The base capacitance can be on the order of 5-75 pF and the resulting pulse-waveform signal (from the pulse-wave events) can have a maximum amplitude on the order of 0.1 to 1 pF. However embodiments are not so limited and such values can be revised for different applications through the sensor and electronic designs.

The relative changes in capacitance over a period of time can be used to generate and/or otherwise output a pulse-waveform signal. The pulse-waveform signal can be indicative of the hemodynamic parameters and/or can include an arterial pulse-wave (or sometimes referred to as an "arterial pressure wave"). The changes in capacitance that are attributable to the pulse-wave events can be used to determine hemodynamic parameters, such as various hemodynamic parameters. As may be appreciated by one of ordinary skill in the art, an arterial pulse-waveform is a wave shape generated by the heart when the heart contracts and the wave travels along the arterial walls of the arterial tree. Generally, there are two main components of this wave: a forward moving wave and a reflected wave. The forward wave is generated when the heart (ventricles) contracts during systole. This wave travels down the large aorta from the heart and gets reflected at the bifurcation or the "cross-road" of the aorta into 2 iliac vessels. In a normal healthy person, the reflected wave can return in the diastolic phase, after the closure of the aorta valves. The returned wave has a notch and it also helps in the perfusion of the heart through the coronary vessels as it pushes the blood through the coronaries. The velocity at which the reflected wave returns becomes very important: the stiffer the arteries are, the faster it returns. This may then enter into the systolic phase and augment final blood pressure reading. The arterial pulse-wave travels faster than ejected blood.

The example apparatus illustrated by FIG. 1A (as illustrated by FIG. 1B) can be modified in a variety of ways, such as illustrated by FIG. 1B. One example modification includes modifying the electrode 102 to be electrically insulated from the skin of the user. The electrode 102 can be insulated by adding a dielectric layer to a portion of and/or surrounding (e.g., encapsulating) the electrode 102. In some specific embodiments, the electrode 102 can be connected to circuitry (e.g., a sensor circuit, such as a circuit board or chip) that is contained in a wristband. The electrode 102 can be flexible. For example, the electrode 102 can be bent around and hidden inside the wristband while worn by a user. In other examples and/or in addition, the electrode 102 can be integrated and/or embedded into the wristband. The dielectric layer can be formed of a variety of different dielectric (or insulating) materials, such as polyester (e.g., polyethylene terephthalate), polyolefin, fluoropolymer, polyimide, polyvinylchloride, cellulose, paper, cloth, and/or other insulating material. Further, the dielectric layer can have different thicknesses, such as on the order of 5 to 250 microns. Although embodiments are not so limited, and the dielectric layers can be thicker or thinner to affect the stiffness and/or comfortability of wearing the apparatus for the user or to modulate the sensitivity of the sensor circuit 103.

The shape of the pulse-waveform can be different for different users and/or based on the location of the measurement. For example, a wider pulse pressure can suggest or be indicative of aortic regurgitation (as in diastole, the arterial pressure drops to fill the left ventricle though the regurgitating aortic valve). A narrow pulse pressure can be indicative of cardiac tamponade, or any other sort of low output state (e.g., severe cardiogenic shock, massive pulmonary embolism or tension pneumothorax). Further, the shape of the pulse-waveform can adjust depending on the location of the measurement, such as the further away the measurement is from the aorta (e.g., the brachial artery, the radial artery, the femoral artery, and the dorsalis pedis). However, with the changes in shape of the waveform, Mean Arterial Pressure (MAP) may not change and/or changes within a threshold amount. This is because, from the aorta to the radial artery, there is little change in the resistance to flow. MAP begins to change once the location is moved to the arterioles. The change in shape from the aorta location to the dorsalis pedis can include an increase in systolic peak, dicrotic notch that is further away from the systolic peak, lower end-diastolic pressure (e.g., wider pulse pressure), and later arrival of the pulse (e.g., sixty second delayed in radial artery from aorta). The resulting shape is sometimes called distal systolic pulse amplification as the systolic peak is steeper and further down the arterial tree.

Embodiments in accordance with the present disclosure are used to output pulse-waveforms and to determine various hemodynamic parameters using an apparatus including a wearable apparatus including a sensor circuit that is non-invasive. The apparatus can be used to monitor heart rate, diastolic blood pressure, systolic blood pressure, arterial stiffness, blood volume, and other parameters. Previous invasive apparatuses, such as an arterial line, are medically inserted into a user, which can be painful, restricts patient movement, and can put the user at risk for infection and other complication. For example, an arterial line is a thin catheter inserted into an artery of the user. Often the catheter is inserted into the radial artery of the wrist but can also be inserted into the brachial artery at the elbow, the femoral artery in the groin, the dorsalis pedis artery in the foot, and/or the ulnar artery in the wrist. Arterial lines can be used in intensive care medicine and anesthesia to monitor blood pressure directly and in real-time. As insertion can be painful, an anesthetic (e.g., lidocaine) can be used to make the insertion more tolerable and to help prevent vasospasm. Complications from arterial lines can lead to tissue damage and even amputation. The apparatus in accordance with the present disclosure can be used to monitor blood pressure in real-time in a non-invasive manner. The apparatus can avoid and/or mitigate risk caused by invasive devices, such as temporary occlusion of the artery, pseudoaneurysm, hematoma formation or bleeding at the puncture sites, abscess, cellulitis, paralysis of the median nerve, suppurative thrombarteritis, air embolism, compartment syndrome and carpal tunnel syndrome, nerve damage, etc.

As illustrated by FIG. 1B, various characteristics can be revised to adjust the sensitivity of the apparatus and/or improve signals obtained by the electrode. FIG. 1B illustrates an example apparatus comprised of a plurality of electrodes 102-1, 102-2, and 102-3. Each electrode 102-1, 102-2, 102-3 is used to sense pressure or capacitance changes attributable to pulse-wave events (e.g., caused by changes in distance between an electrode and the skin surface), as previously described. The electrodes 102-1, 102-2, and 102-3 can be part of or form a transducer circuit 110 that provides the one or more signals to the electrical-signal sensing circuit 106. The electrodes 102-1, 102-2, and 102-3 can be placed at different locations of the apparatus to improve positional accuracy and/or to provide one or more reference signals for differential analysis. In some embodiments, each electrode 102-1, 102-2, 102-3 provides a signal indicative of pressure or capacitance changes (attributable to pulse-wave events) to the electrical-signal sensing circuit 106. In specific embodiments, the transducer circuit 110 can have a floating ground. In other specific embodiments, at least one of the sensor circuits has a floating ground (e.g., two sensor circuits, each having floating grounds, all the sensor circuits with each having floating grounds, etc.) Further, both the transducer circuit 110 and at least one of the sensor circuit can have a floating ground.

Although FIG. 1B (as well as other illustrations including but not limited to FIGS. 2A, 2B and 2D) does not illustrate a sensor circuit connected to the electrode and/or a sensor circuit connected to each of the plurality of electrodes, one of ordinary skill may appreciate that in accordance with various embodiments, each electrode is connected to a sensor circuit, as previously described. In this manner, the illustration of FIG. 1B, as well as other illustrations, does not show the sensor circuit for clarity purposes and which is not intended to be limiting.

In various embodiments, the apparatus (e.g., the electrical-signal sensing circuit 106) can further include a wireless communication circuit. The wireless communication circuit wirelessly communicates data from the electrical-signal sensing circuit 106 to circuitry that is external from the apparatus. The communication circuit can be configured and arranged to communicate the captured changes attributable to the hemodynamic pulse wave events to external processing circuitry. The communication circuit may be within or outside the wearable device and/or apparatus, and may respond to the electrical-signal sensing circuit by sending hemodynamic-monitoring data to an external circuit. Further, the apparatus can include a power supply circuit 112, as further described herein.

In some embodiments, one or more of the plurality of electrodes 102-1, 102-2, 102-3 can be electrically insulated from the skin of the user. As described above, the electrodes 102-1, 102-2, 102-3 can be insulated by adding a dielectric layer 108-1, 108-2, 108-3 to some or all of the plurality of electrodes 102-1, 102-2, 102-3. The dielectric layers 108-1, 108-2, 108-3 can surround each of the electrodes 102-1, 102-2, 102-3 and/or the respective sensor circuits. However, embodiments in accordance with the present disclosure are not so limited and can include a dielectric layer that is position at a portion of and/or area of the electrode that is arranged to contact the skin surface, and/or surrounds at least part of the respective electrode or the sensor circuits.

The transducer circuit 110, as illustrated by FIG. 1B, can be used to provide a differential mode to subtract out artifacts. The artifacts can be baseline shifts due to motion of the user, such as limb movement, breathing and/or changes in body temperature. In various embodiments, the different electrodes 102-1, 102-2, and 102-3 of the transducer circuit 110 have different structural properties and/or characteristics used to modify the sensitivity level of the respective sensor circuit that includes the electrode. For example, the electrodes 102-1, 102-2, and 102-3 can be different shapes (e.g., geometries), be positioned at different locations with respect to the user and/or the apparatus, and can be formed of different materials. In other embodiments, the different structural properties and/or characteristics can include different compositions, structural components, textures, and/or thickness of the encapsulants used to electrically isolate the electrodes. For example, the dielectric layers of respective electrodes 102-1, 102-2, 102-3 can be formed of dielectric material of different compositions, structures, and/or thickness to modify the sensitivity levels and/or shielding features used to isolate the electrodes. Thereby, the plurality of electrodes may have encapsulants configured and arranged to set a sensitivity level of each of the plurality of electrodes.

In various embodiments, the apparatus further includes a power supply circuit 112. The power supply circuit 112 provides power to at least the electrical-signal sensing circuit 106. In some specific implementations, the power supply circuit 112 is a passively or inductively powered circuit, such as an inducer circuit. Example power supply circuits include a battery, solar power converter, electromechanical systems, a wall plug-in (e.g., mains electricity), among other sources of power.

Figures 2A, 2B, 2C, 2D:
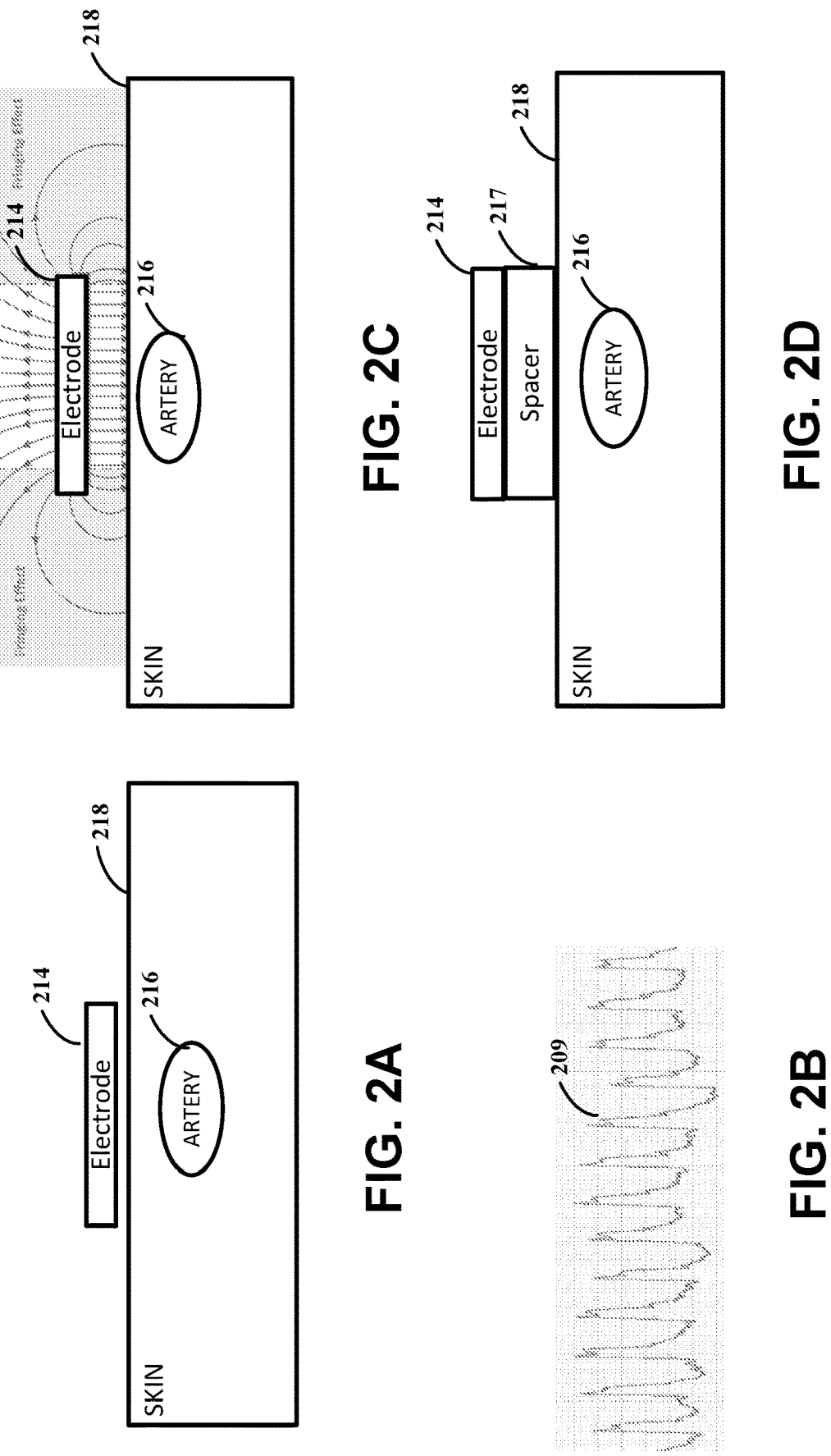
FIGS. 2A-2D illustrate an example of an apparatus and the resulting interaction with the skin of a user, in accordance with the present disclosure.

FIG. 2A illustrates an example of an apparatus including a sensor circuit having an electrode 214 that interacts with skin 218. As previously described, the sensor circuit and electrode can carry capacitance changes through proximity sensing of the skin of the user (as opposed to physically deforming as a capacitance sensor), and thereby acts as or is a proximity sensor. It has been discovered that a (proximity) sensor circuit with a single electrode 214 placed near an arterial pulse point (e.g., artery 216) can be used to measure the arterial pulse-waveform via the capacitance changes. Heart rate and other hemodynamic parameters may be extracted from this waveform. The electrode 214 can be in direct contact with the skin 218 or electrically insulated or isolated from the skin 218. It does not need to be mechanically coupled to the skin 218. The composition, structure and thickness of the electrical insulation can be chosen to modify the sensitivity of the sensor. Spacer structures can be used to control the distance between the electrode and the skin. The circuit may have a floating ground (e.g., the sensor circuit and/or transducer circuit can have a floating ground).

Arrays of electrodes can also be used to improve positional accuracy and/or to provide reference signals for differential analysis. And, the signal can be improved through electrode designs that optimize the fringe field distribution. For example, in some embodiments, analog responses are sensed by the array of sensor circuits, with each sensor circuit having a single electrode. The two or more of the electrodes in the array can have different sensitivity levels and the analog responses sensed by the two or more sensor circuits of the arrays can be used for differential sensing.

FIG. 2B illustrates an example of a pulse-waveform 209 that is sensed using the apparatus illustrated by FIG. 2A. As illustrated, the periodicity of the pulse-waveform 209 reflects the cardiac cycle and can be used to determine a heart rate of the user.

FIG. 2C illustrates an example mechanism for an apparatus to monitor pulse-wave events. As illustrated by FIG. 2C, the skin 218 of the user serves as the ground plane for the mechanism. Without constraint to a particular theory, it is believed that the mechanisms behind aspects of one or more of the embodiments discussed in the disclosure are as follows: (i) the skin 218 serves as a ground plane and arterial pressure variations cause displacement of the surface of the skin 218, and this changes the distance between the electrode 214 and the skin 218 which is measured as a change in capacitance; (ii) the potential of the blood in the artery 216 (and the overlying skin) changes with each heartbeat, and this modifies the fringe field lines which is reflected as a change in impedance; and (iii) a combination (contribution) from each of the above mechanisms is involved.

FIG. 2D illustrates an example of an apparatus, as illustrated by FIG. 2C, which further includes one or more spacers that set the distance (e.g., the minimum distance) between at least a portion of the sensor circuit (e.g., the electrode 214) and the skin 218. The spacer 217 includes one or more structures formed of a material, in which the length (e.g., the distance from the electrode to the skin surface) sets the distance between at least a portion of the sensor circuit/electrode and the skin. The length can be in a range of 0.1 millimeter (mm) to 1.0 mm, although embodiments are not so limited. Although the embodiment of FIG. 2D illustrates one spacer having rectangular shape, embodiments are not so limited and can include more than one spacer and different shaped spacers, such as a layer of textured and/or structured material.

Figure 3:
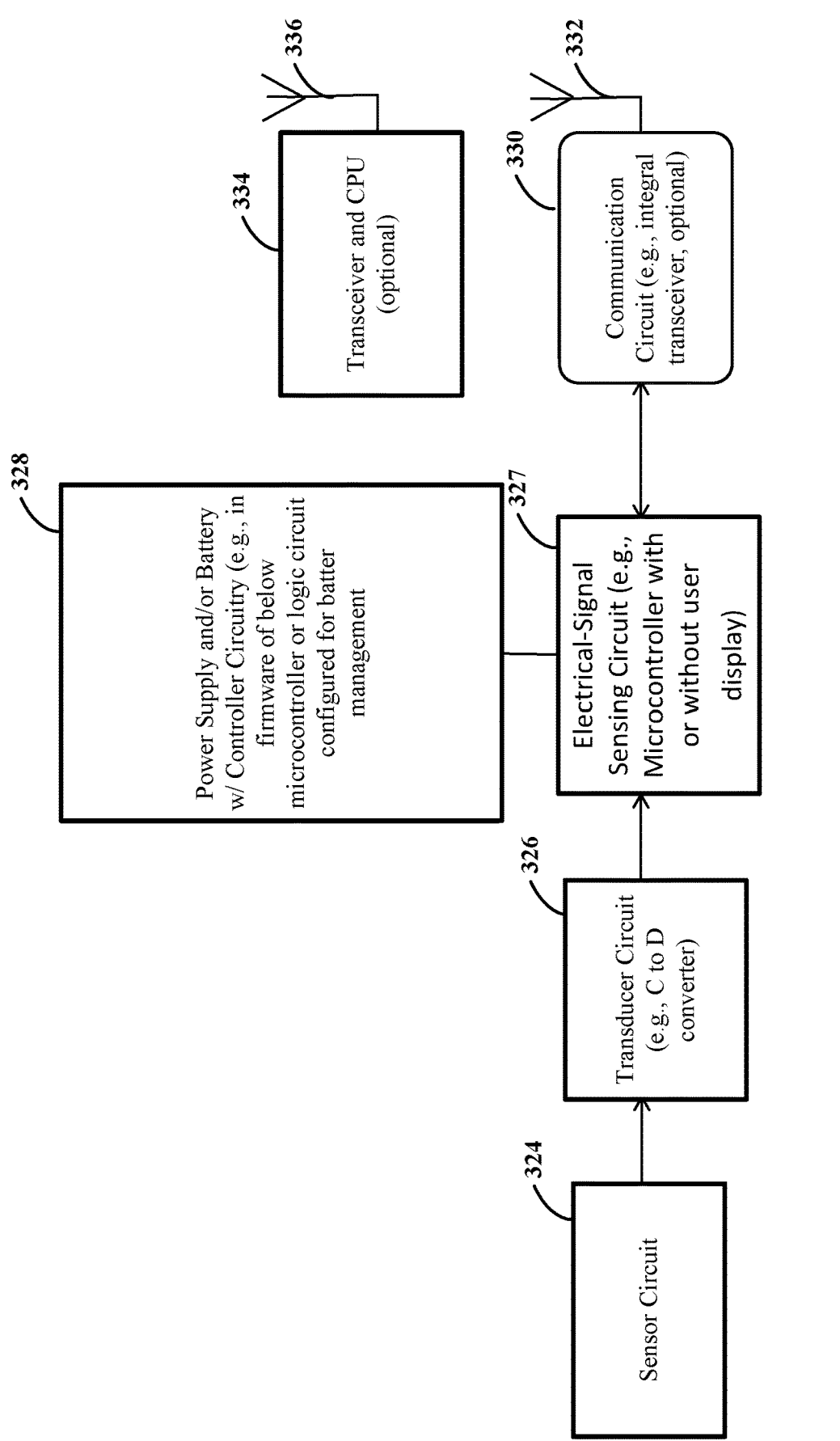
FIG. 3 is a block diagram that exemplifies an example way for implementing the electronics and/or signal flow from the apparatus, in accordance with the present disclosure.

FIG. 3 is a block diagram that exemplifies an example way for implementing the electronics and/or signal flow, from the apparatus (including, e.g., sensor circuit 324, transducer circuit 326, electrical-signal sensing circuit 327 and communication circuit 330) situated at or near the user's skin to a remotely/wirelessly-communicative transceiver and CPU 334 (e.g., received via antenna 336), in accordance with the present disclosure. The CPU 334 and/or electrical-signal sensing circuit 327 can be programmed to carry out operations as disclosed herein including without limitation: processing the raw data for indicating the presence of specific hemodynamic signals, developing waveforms from the raw data, and/or evaluating the integrity, quality and relevance of the hemodynamic signals and/or waveforms for specific applications pertinent to the user's hemodynamic state or well-being (the user's heart rate or other hemodynamic indicators or parameters such as diastolic blood pressure, systolic blood pressure, arterial stiffness, and blood volume, and/or indicative of changes in one or more of the indicators or parameters).

The electrode of the sensor circuit 324 captures capacitance changes responsive to pulse-wave events and provides the capacitance changes to a transducer circuit 326. In some embodiments, the transducer circuit 324 is or includes a capacitance-to-digital converter. The capacitance-to-digital converter converts the capacitance values (e.g., the relative changes) to a digital signal and outputs the digital signal to the electrical-signal sensing circuit 327, which can include or be a microcontroller or other processing circuitry. The electrical-signal sensing circuit 327, using power provided by the power supply 328, measures and/or records an arterial pulse-waveform and optionally conditions the signal, evaluates the quality of the data, and/or determines one or more hemodynamic parameters. The electrical-signal sensing circuit 327 can output the waveform and other optional data to the CPU 334 via the communication circuit 330 (e.g., the integral transceiver) and antenna 332.

The sensing apparatuses, as described herein, can be used to monitor pulse-wave events in a hands-free manner and without interference from environmental noise (e.g., human voices and other background noise, electrical interference, and/or ambient light). Moreover, the electrical-signal sensing circuit can sense the hemodynamic or pulse-wave events in response to electrical signals from the transducer circuit. The electrode (or array of electrodes) can consume relatively low amounts of power (e.g., between (less than) 5 microwatts and 3 milliwatts). In some specific embodiments, the power consumption can be further reduced by only saving data after a trigger event and/or transmitting saved data in burst transmissions. Trigger events can include particular heart events that may be indicative of a problem, such as heart rates above or below a threshold amount and/or particular waveform characteristics.

Figures 4A, 4B:
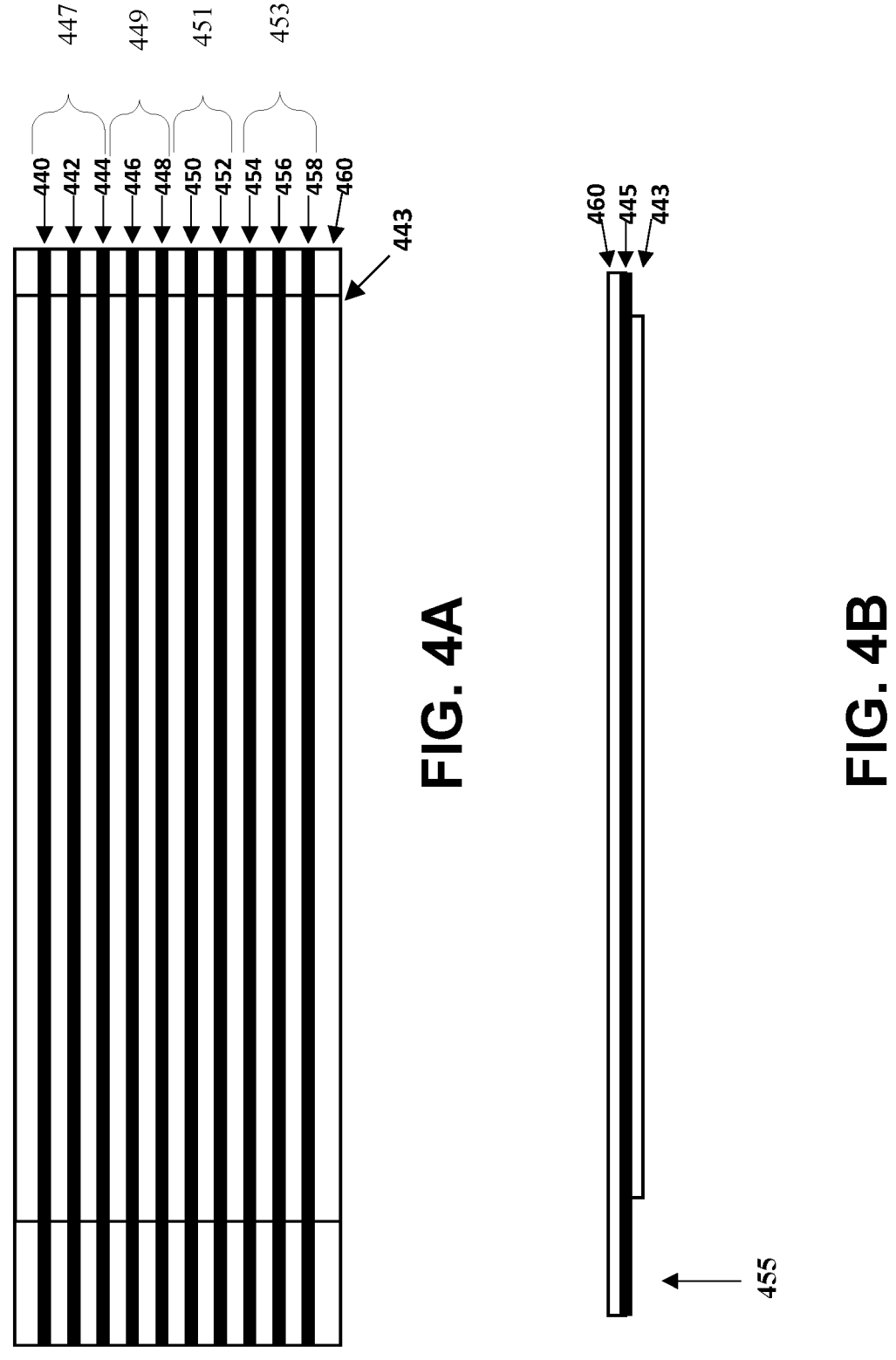

FIGS. 4A-5B illustrate various example apparatuses having an array of sensors, in accordance with the present disclosure. For example, FIGS. 4A-4B illustrate an example apparatus with four electrodes configured to interact with skin of the user.

FIG. 4A illustrates a top-down (or birds-eye) view of an apparatus comprised of a sensor array having four sensor circuits including four electrodes 447, 449, 451, 453. The line widths and spacings can be on the order of 0.1 mm to 20 mm for pulse monitoring applications. As illustrated, the sensor array includes optional ground connections 440, 458 and optional active shield connection 442,448, 450, 456. The array of sensors further includes sensor connections 444, 446, 452, 454 and insulation layers 460, 443.

FIG. 4B illustrates a side view of the apparatus illustrated by FIG. 4A. As illustrated, the layers include the insulating layer 460, the four electrodes 445 (e.g., the electrodes 447, 449, 451, 453 illustrated by FIG. 4A), and another insulating layer 443. The apparatus includes an active portion (or region) 455 configured to be in proximity to or in contact with the skin of a user or other subject. The length of the active portion 455 can be on the order of 0.1 mm to 20 mm or more for pulse monitoring applications. Further, the active portion 455 can be in contact with the skin or not in contact and up to a distance of 1 mm away from the skin. In various specific embodiments, the distance is typically less than 100 microns from the skin, which can be a distance sufficient to obtain signals having resulting signal-to-noise values that are low enough to obtain heart rate and/or blood pressure therefrom. In specific embodiments, the electrodes 445 can be textured or corrugated for sensitivity purposes and to reduce the contact with the skin. Smaller active areas may have higher sensitivities but can be difficult to position accurately.

In various embodiments, the apparatus include a packaged array of sensors including the (four) electrodes 445 configured to interact with the skin of the user. The array of sensors (e.g., the electrodes) can be packaged in insulating material (e.g., dielectric material) to provide environmental stability and resistance to moisture. The insulating material can include polyester, polyolefin, fluoropolymer, polyimide, polyvinylchloride, cellulose, paper, cloth, among other material. The packaging thickness can be on the order of 5 to 250 microns or more. Similarly, optional adhesive and conductive layer thicknesses can be on the order of tens of microns, and typically less than 70 and 5 microns for adhesive and the conductive layer respectively. The conductive layer(s) can optionally be passive shielding layers and/or connected to the control electronics to provide active shielding.

Figure 5A:
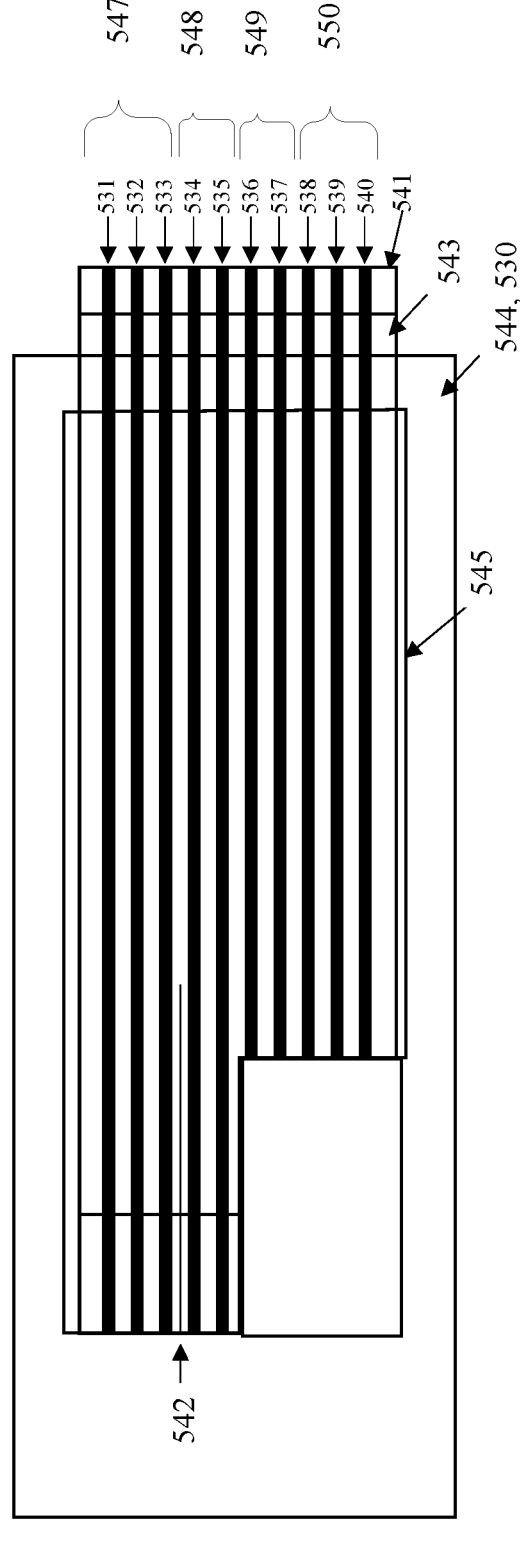
Figure 5B:
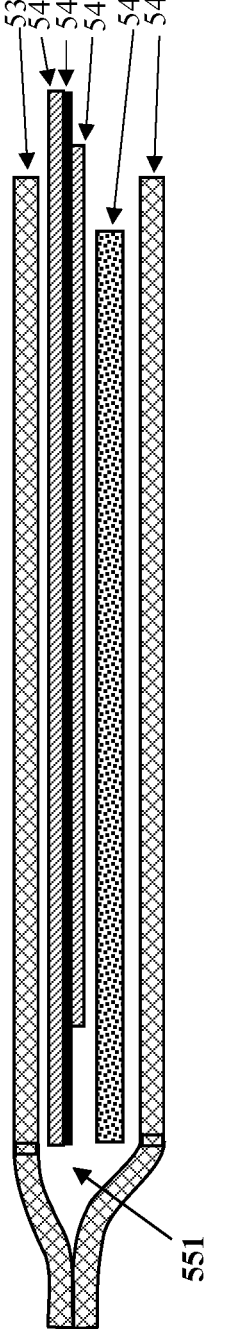

In specific embodiments, the layers include the insulating layer with optional shielding and adhesive coatings, an insulating layer, one or more electrodes, another insulating layer, and another insulating layer with optional shielding and adhesive coatings, as further illustrated and discussed herein in connection with FIGS. 5A-5B.

In some embodiments, the array of sensors (e.g., the electrodes) can be packaged in insulating material (e.g., dielectric material) to provide increase environmental stability and resistance to moisture. One or more insulating layers can be slit at one or more locations to mechanically isolate individual sensor circuits and to increase the conformability of the packed sensors to the underlying substrate.

In further specific embodiments, the packaged array of sensors include the (four) electrodes 445 and a spacer layer. The spacer layer includes one or more spacers that can set or control a distance of the sensor circuits and/or the electrodes (or at least a portion thereof) from the skin surface, as previously illustrated by FIG. 2D. The spacer layer can minimize or mitigate stray capacitance from non-active (non-sensor) regions. The spacer layer thickness can be on the order of 0.1 mm to 5 mm or more, so long as the distance does not impact sensor sensitivity. The array of sensors (e.g., the electrodes) can be packaged in insulating material (e.g., dielectric material) to provide environmental stability and resistance to moisture. The packaging thickness can be on the order of 5 to 250 microns or more. Similarly, optional adhesive and conductive layer thicknesses can be on the order of tens of microns, and typically less than 70 and 5 microns for adhesive and the conductive layer respectively.

The packaged array of sensors can further include a shield layer. As further described below, one or more insulation layers can have an adhesive coating on its inner surface such that the layer adheres to other layers, such as adhering the insulation layer to another insulation layer(s). The insulation layer can have a conductive layer on its outer surface that contacts the skin of the user. The conductive layer may alternatively be sandwiched between two insulating layers. The conductive material can include, for example, aluminum, gold, carbon, or copper that has been printed, evaporated, sputtered, or plated onto a non-conductive substrate (e.g., of PET or polyimide substrate). The insulating layers can be slit at one or more locations to mechanically isolate individual sensor circuits and to increase the conformability of the packaged sensor circuits to the underlying substrate. Thereby, the substrate can be configured and arranged as a user accessory conforming to the user's wrist, limb, or other body portion.

In a specific experimental embodiment, the insulating layers 443, 460 and the electrodes 445 are formed of flexible flat cable (FFC/FPC) cable (such as commercially available Molex 15168-0147), the insulating layer 460 with the adhesive coating is formed of Polyethylene terephthalate (PET) with an adhesive (such as commercially available Avery 15660), the insulating layer 443 with a conductive material is formed of 12 micron PET with around or greater than 2 optical density evaporated aluminum (such as commercially available Celplast Cel-Met 48 g) and the spacer layer is formed of a layer of foam tape (such as commercially available Nexcare 731). Individual electrodes can be 0.625 mm wide with 0.625 mm spaces between them.

The different electrodes 445 can have different capacitive sensitivities. The apparatus can include a spacer layer that covers active portions of some sensor circuits but not all sensors. The sensor circuits may have isolated electronics for readouts to prevent or mitigate crosstalk through a common circuit.

The flexibility or degree of bending of the sensor circuits as illustrated throughout this disclosure (e.g., including FIGS. 1A-1B, 2A, 2C-2D, 4A-4B, 5A-5B, 6B, and 16) can be sufficient to capture the changes in pressure or capacitance (e.g., a change in capacitance values). More specifically, the degree of stiffness of the sensor circuit is inversely proportional to the thickness and/or length of the sensor circuit (e.g., the thicker or longer the electrode, the stiffer). Flexibility and thickness (and/or length) can be configured relative to one another sufficient to provide a sensitivity to pressure changes of 0.3 kilopascal (kPa) to 1 kPa and/or capacitance changes in a range of plus and minus 15 picofarad (pF) from a base capacitance of the sensor circuit. In more specific embodiments, the flexibility and thickness and/or length can be configured relative to one another sufficient to provide a sensitivity to pressure changes of 0.5 kPa to 1 kPa. Further, as described herein, the measurement of changes in pressure, which are indicative of a change in capacitance, can be sensed when the sensor circuit is touching the skin or other surface. The sensed change in capacitance can be obtained when the electrode(s) are not contacting the skin or other surface of the user (but are within 1 mm away).

FIGS. 5A-5B illustrate an example apparatus having a packaged array of sensors including a plurality (e.g., four) of electrodes having different capacitive sensitivities. The apparatus includes a spacer layer 545 that covers active portions of some sensor circuits (e.g., electrode 547 and 548) but not all sensor circuits (e.g., not electrodes 549 and 550). Alternatively and/or in addition, some of the sensor circuits (e.g., electrodes 549 and 550) and portions of the insulating layers 541, 543 are a shorter length than the remaining sensors (e.g., electrodes 547, 548) (with respect to the end of the apparatus proximal to the active portion 551). The sensor circuits may have isolated electronics for readouts to prevent or mitigate crosstalk through a common circuit. As previously described, one or more insulation layers 530 can have an adhesive coating on its inner surface such that the insulating layer 530 adheres to other layers, such as adhering the insulation layer 530 to other insulation layers 541, 544. The other insulation layer 544 can have a conductive layer on its outer surface that contacts the skin of the user.

FIG. 5A illustrates a top-down (or birds-eye) view of the apparatus comprised of four electrodes 547, 548, 549, 550. As illustrated, the sensor array includes optional ground connections 531, 540, and optional active shield connections 532, 535, 536, 539. The array of sensors further includes sensor connections 533, 534, 537, 538, insulation layers 541, 543, a spacer layer 545, and additional insulation layers 544, 530 with optional shielding and adhesive coatings. The insulating layers 541, 543 can be slit at one or more location(s) 542 to mechanically isolate individual sensor circuits and to increase the conformability of the packed sensors to the underlying substrate.

FIG. 5B illustrates a side view of the apparatus illustrated by FIG. 5A. As illustrated, the layers include the insulating layer 530 with an adhesive coating on the inner surface (e.g., on the surface proximal to the insulating layer 541), insulating layer 541, the four electrodes 546 (e.g., the electrodes 547, 548, 549, 550 illustrated by FIG. 5A), another insulating layer 543, spacer layer 545, and another insulating layer 544 with a conductive material on the outer surface (e.g., on the surface that is opposite and/or not proximal to the spacer layer 545). The apparatus includes an active portion 551, as previously described.

Figures 6A, 6B, 6C:
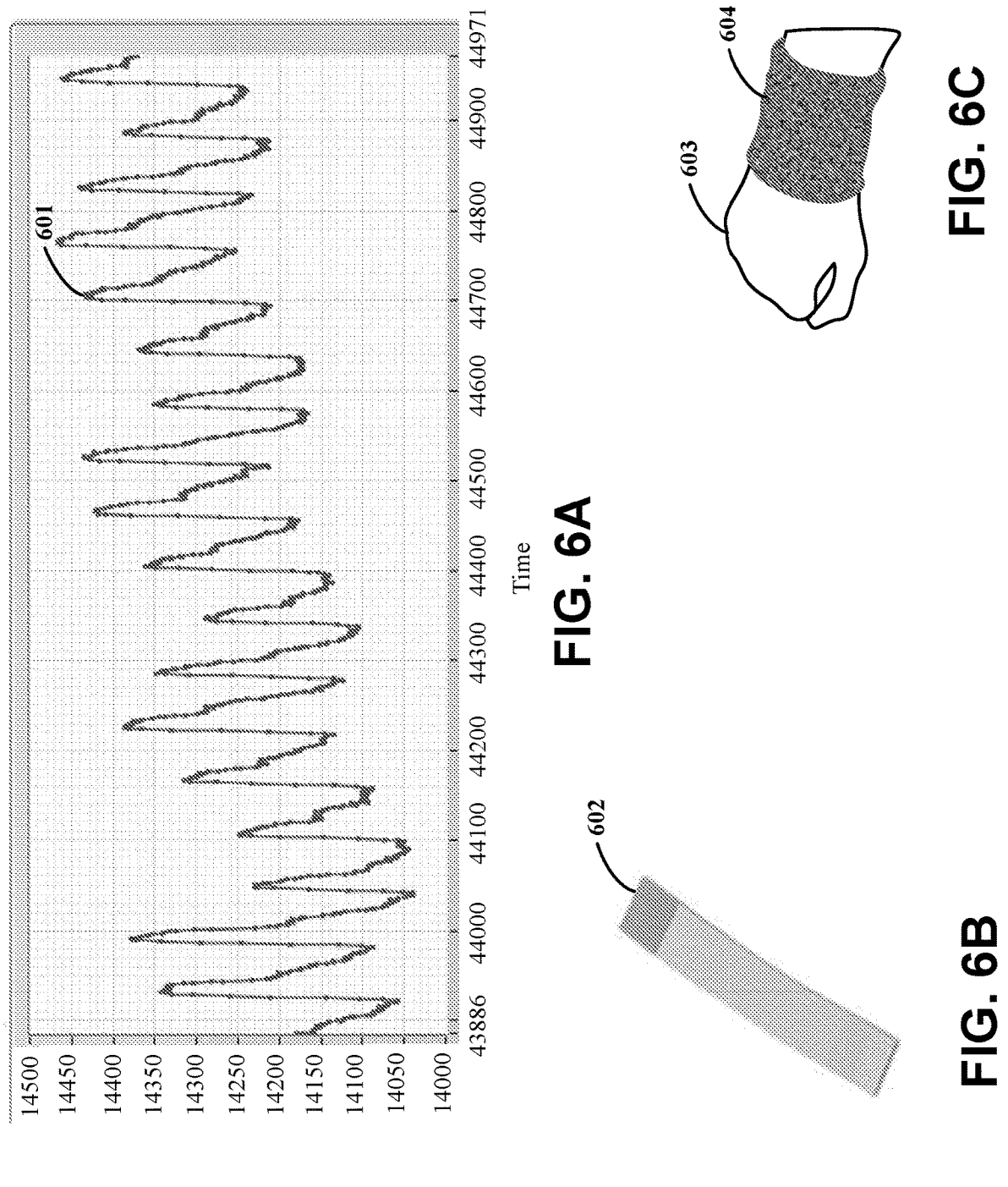
FIGS. 6A-6C illustrate an apparatus, in accordance with the present disclosure.

FIGS. 6A-6C illustrate an apparatus, in accordance with the present disclosure. In certain embodiments, as illustrated by FIGS. 6B and 6C, the apparatus can have a flex ribbon sensor array 602 configured and arranged to sense pulse-waveforms. The flex ribbon sensor array 602 can be held in pace with a wristband 604, as illustrated by FIG. 6C, that can be placed around a wrist of a user 603. The chart illustrated by FIG. 6A shows capacitance data for a characteristic radial arterial pulse-waveform shape 601. In an example experimental embodiment, a bandpass filter (20 Hz/0.5 Hz) is used to process the data, resulting in a calculated heartrate that is 71 bpm. The reference heartrate (from a Fitbit Charge HR™) is 70 bpm, which demonstrates that the sensor signal is reflective of the cardiac cycle. For this embodiment, the flex ribbon sensor array 602 is held by an elastic wristband 604 to contact flat next to the user's skin. A Molex 15168-0147 FFC jumper cable can be used as the flex ribbon sensor array, in various embodiments. The heartrate can be calculated from a Fourier transform of such waveform data. The flex ribbon sensor array 602 can be connected to a Bluetooth proximity sensing circuit (e.g., an electrical-signal sensing circuit).

Figure 7:
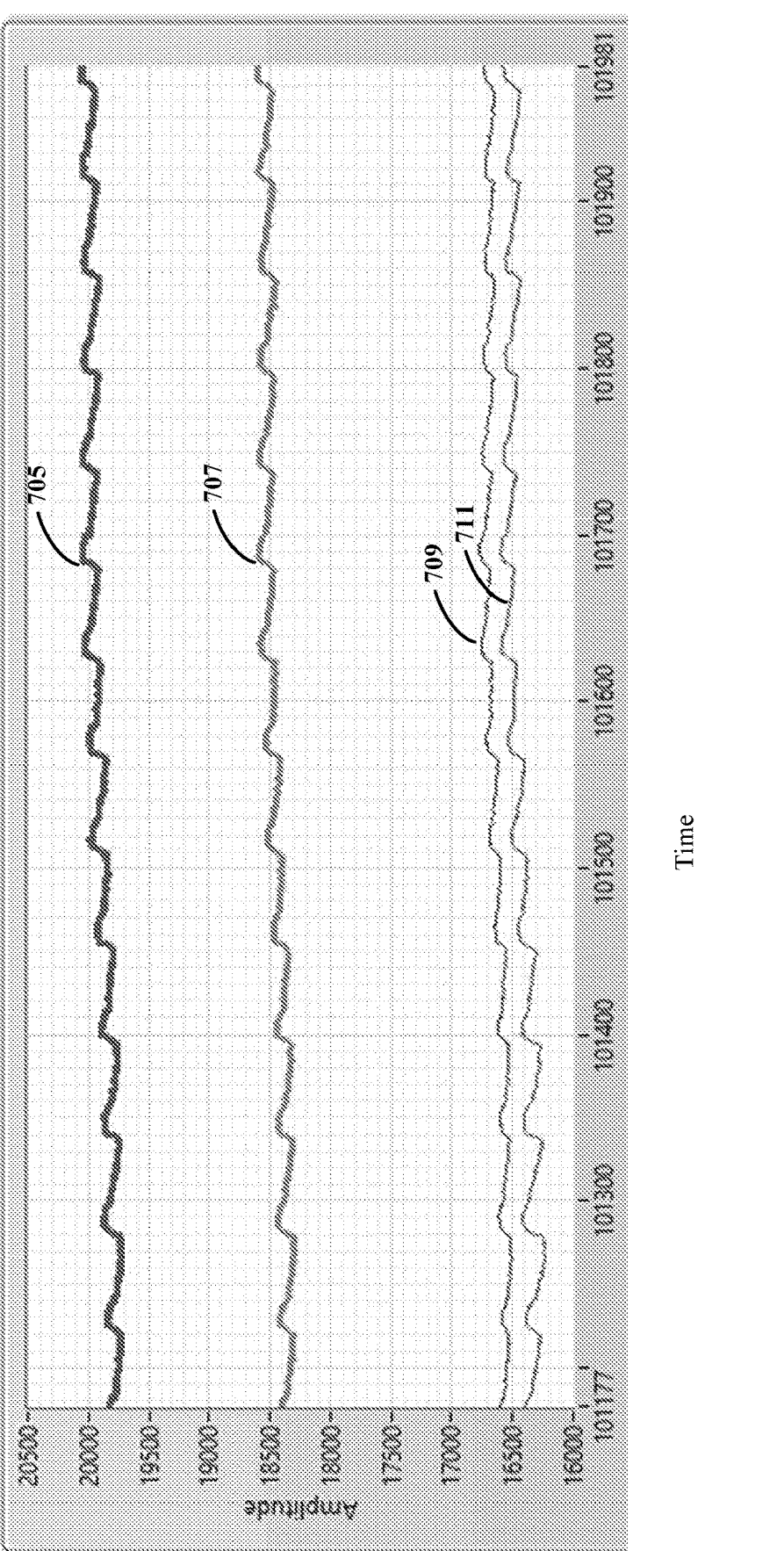
FIG. 7 illustrates example data captured using an apparatus, such as the apparatus illustrated by FIGS. 6B-6C, in accordance with various embodiments.

FIG. 7 illustrates example data captured using an apparatus, such as the apparatus illustrated by FIGS. 6B-6C, in accordance with various embodiments. In certain embodiments, the apparatus can include a ribbon cable which is implemented so that multiple channels can be measured simultaneously (or in the alternative, concurrently or sequentially) along different signal paths respectively provided by the cable's conductive lines. In such embodiments, a different electrode (and the respective sensor circuit) is configured in one of the multiple channels (e.g., signal paths) respectively carrying signals for sequential processing by the electrical-signal sensing circuit and/or for concurrent or simultaneous processing by the electrical-signal sensing circuit. As an example implementation of four channels that can be measured, as illustrated by FIG. 7A, the apparatus can include four electrodes, with each of the four electrodes arranged in a respective signal path/channel. Similarly to FIG. 6A, a bandpass filter (20 Hz/0.5 Hz) is used to extract the data (e.g., from the unfiltered 705, 707, 709, 711 from the four channels). In this experimental embodiment, the calculated heartrate is 71 bpm, and the reference heartrate (Fitbit Charge HR™) is 70 bpm. For this embodiment, the flex ribbon sensor array is held by an elastic wristband to contact flat next to the user's skin. A Molex 15168-0147 FFC jumper cable can be used as the flex ribbon sensor array, in various embodiments. The heartrate can be calculated from a Fourier transform of such waveform data. The flex ribbon electrode can be connected to a Bluetooth proximity sensing circuit (e.g., an electrical-signal sensing circuit).

Figure 8:
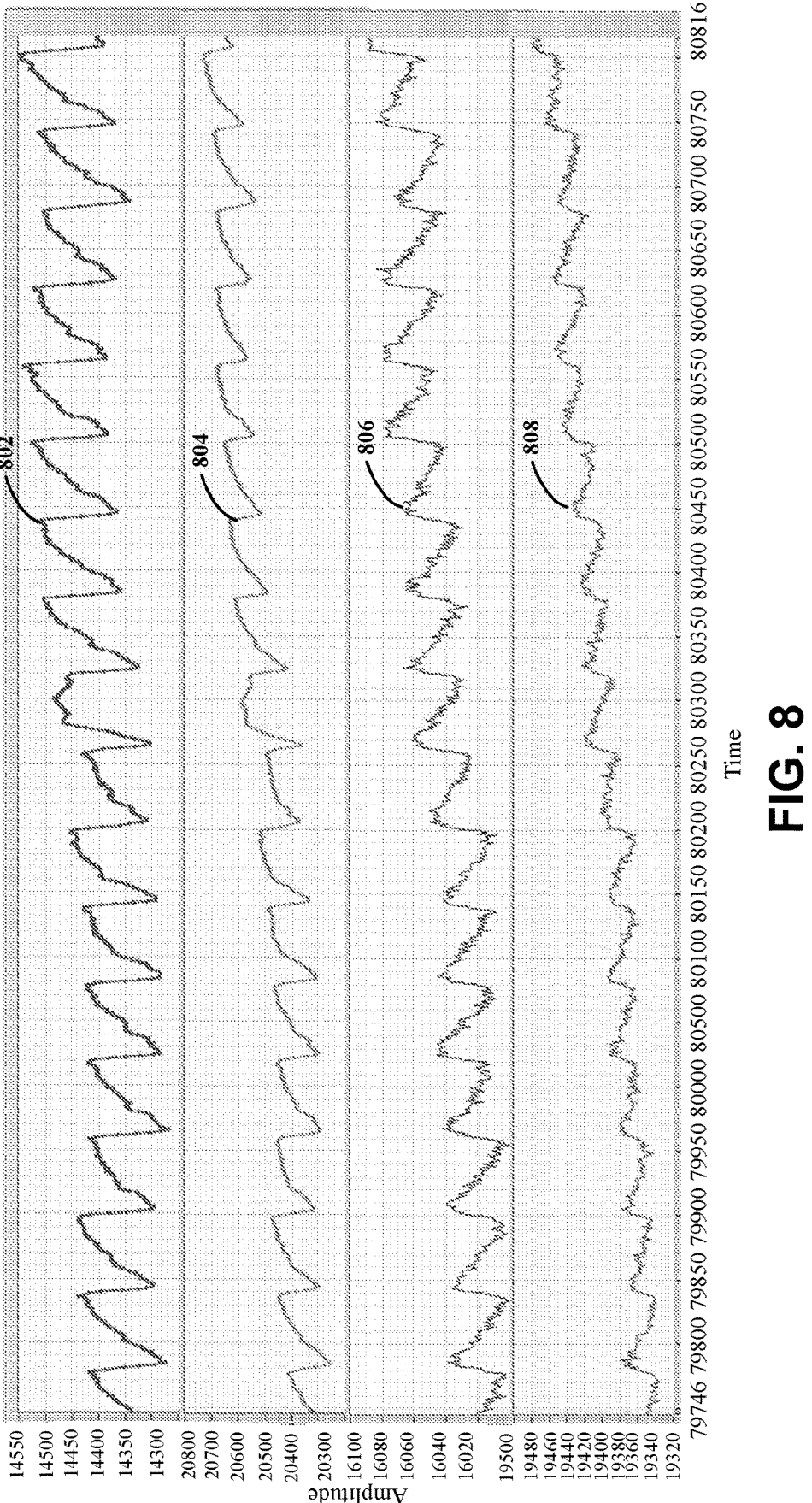
FIG. 8 illustrates example data captured using an apparatus, in accordance with the present disclosure.

FIG. 8 illustrates an example of data 802, 804, 806, 808 captured using an apparatus. In certain embodiments, the apparatus can have additional dielectric insulating layers (tape) for modifying response signal-to-noise. The top two-charts illustrate responses of electrodes with no dielectric insulating layer (e.g., data 802, 804). The bottom two-charts illustrate response of electrodes having one dielectric insulating layer and showing the reduction in signal amplitude (e.g., data 806 and 808).

Figure 9A:
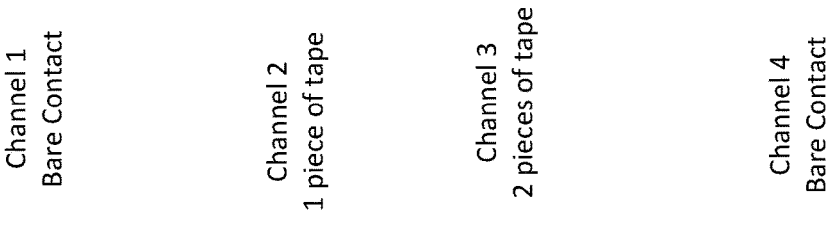
FIGS. 9A-9B illustrate an example apparatus having multiple channels and data captured using the apparatus, in accordance with the present disclosure.
Figure 9B:
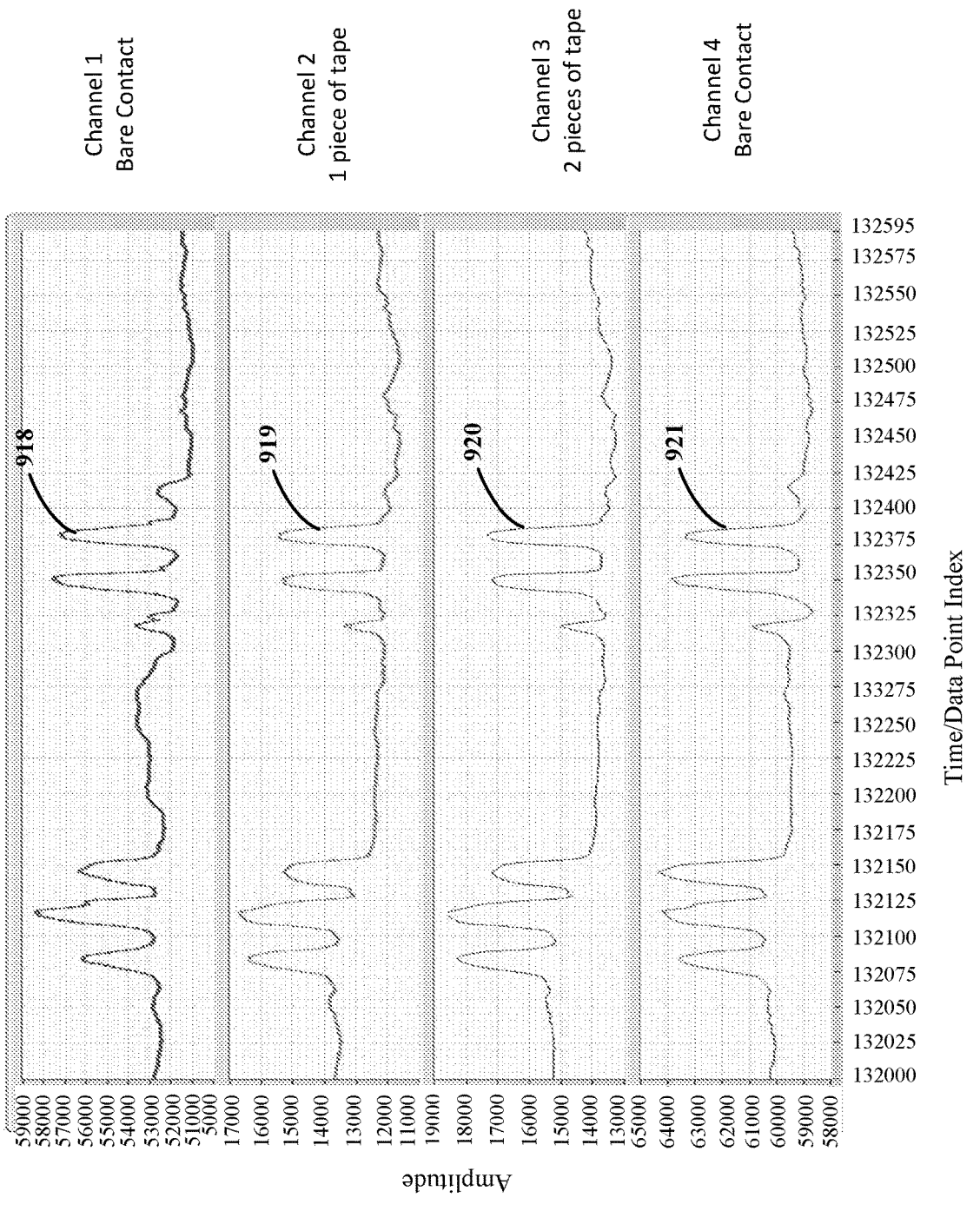

FIGS. 9A-9B illustrate an example apparatus having multiple channels and data captured using the apparatus in various embodiments. One or more of the channels can have or be associated with a dielectric layer(s) which can reduce signal intensity. FIG. 9A illustrates example data captured using an apparatus having four channels (e.g., signal paths in which an electrode is configured in and which respectively carry signals). The amplitude of the signal can be reduced with one or two dielectric layers (e.g., one or two pieces of tape) as compared to a bare contact. As illustrated, the waveform 914 represents data captured using an electrode having no dielectric layer, waveform 915 represents data captured using an electrode having one dielectric layer, waveform 916 represents data captured using an electrode having two dielectric layers, and waveform 917 represents data captured using an electrode having no dielectric layer. The example apparatus used to collect the illustrated data can include a sensor strip that is mechanically coupled to the skin of a user, such as via a wristband.

In certain embodiments, the dielectric layers may modulate the amplitude of the pulse-waveform but may not impede the observation of baseline shifts due to motion or breathing artifacts. FIG. 9B illustrates data captured using the above-described apparatus in response to signal changes caused by a user making up and down motions with their hand and with a 6 inch amplitude. As illustrated, each of the channels is used to capture the observation of baseline shifts due to motion of the user, which is respectively illustrated by the waveforms 918, 919, 920, 921. The sensor circuits with less sensitivity to the pulse-waveform signal (e.g., sensor circuits with one or two layers of dielectric material) may serve as a reference to remove the baseline shifts due to motion of the user in a differential mode.

Figure 10:
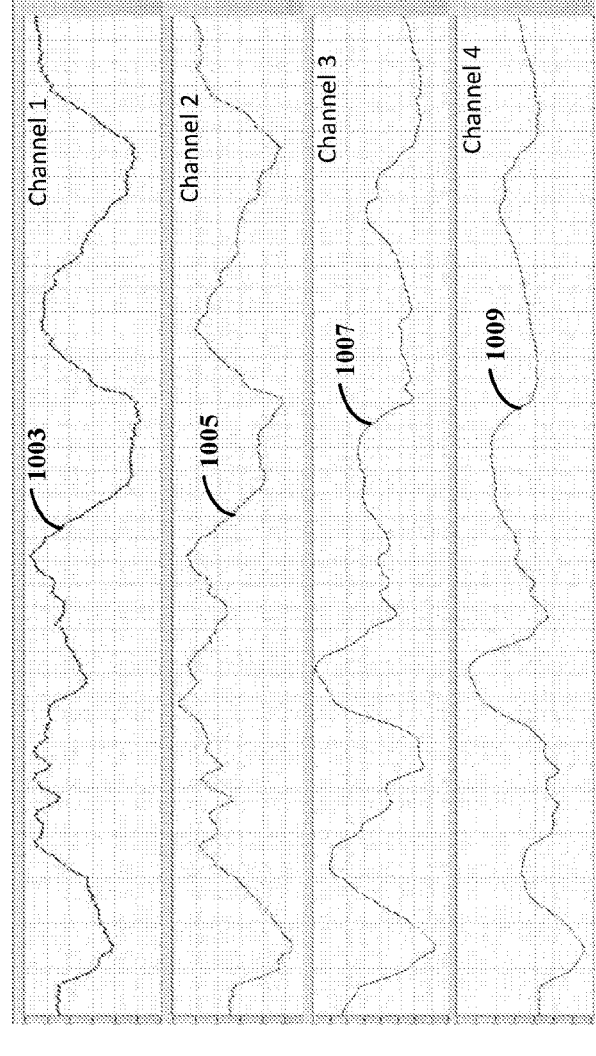
FIG. 10 illustrates example data captured using an apparatus, in accordance with the present disclosure.

FIG. 10 illustrate example data captured using an apparatus, in accordance with various embodiments. Certain embodiments can implement one or more of the electrodes (e.g., sensors) at a variety of locations, such as the front, back, and/or side of the wrist. The location of an electrode at a different location may serve as a reference for gross motion artifacts in a differential mode. The location can be selected to mimic the motion artifacts observed at the pulse point. FIG. 10 illustrates the different data captured using each electrode (e.g., configured in a channel) of the apparatus having four sensor circuits that have been placed in different locations around the wrist. The data captured is represented as waveforms 1003, 1005, 1007, 1009. The sensor circuits can be mechanically coupled to the user via a wristband.

The apparatus, in certain embodiments, can be implemented with different electrode types. For example, FIGS. 11-15B illustrate data captured using different types of electrodes.

Figure 11:
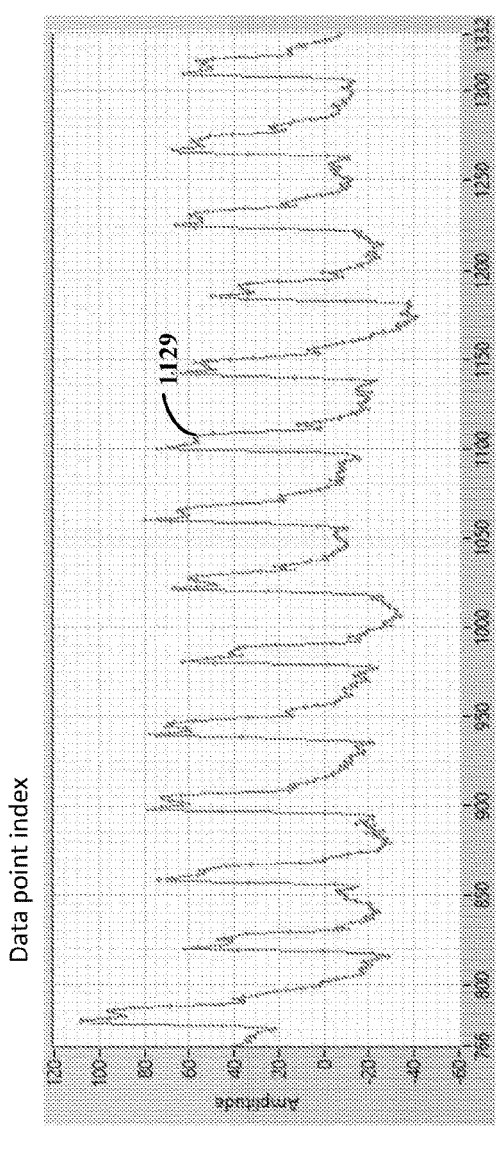
FIG. 11 illustrates example data captured using an apparatus having an electrode with a flat contact, in accordance with the present disclosure.

FIG. 11 illustrates example data captured using an apparatus having a single strip electrode with a flat contact. The data 1129 illustrated by FIG. 11 is unfiltered. A bandpass filter (20 Hz/0.5 Hz) is used to extract the data. In an example experimental embodiment, the calculated HR is 63 bpm, and the reference HR (Fitbit Charge HR™) is 63 bpm. For this embodiment, the copper tape electrode is 6 mm wide and 3 centimeter (cm) long, has a flat copper contact with the user's skin, and is held by an elastic wristband to contact flat next to the user's skin, although embodiments are not so limited. The electrode(s) can be various dimensions, such as in the range of 0.5 mm to 6 mm wide, a range of range of 0.5 mm to 1 cm wide, and 0.5 mm to 3 cm long.

Figure 12:
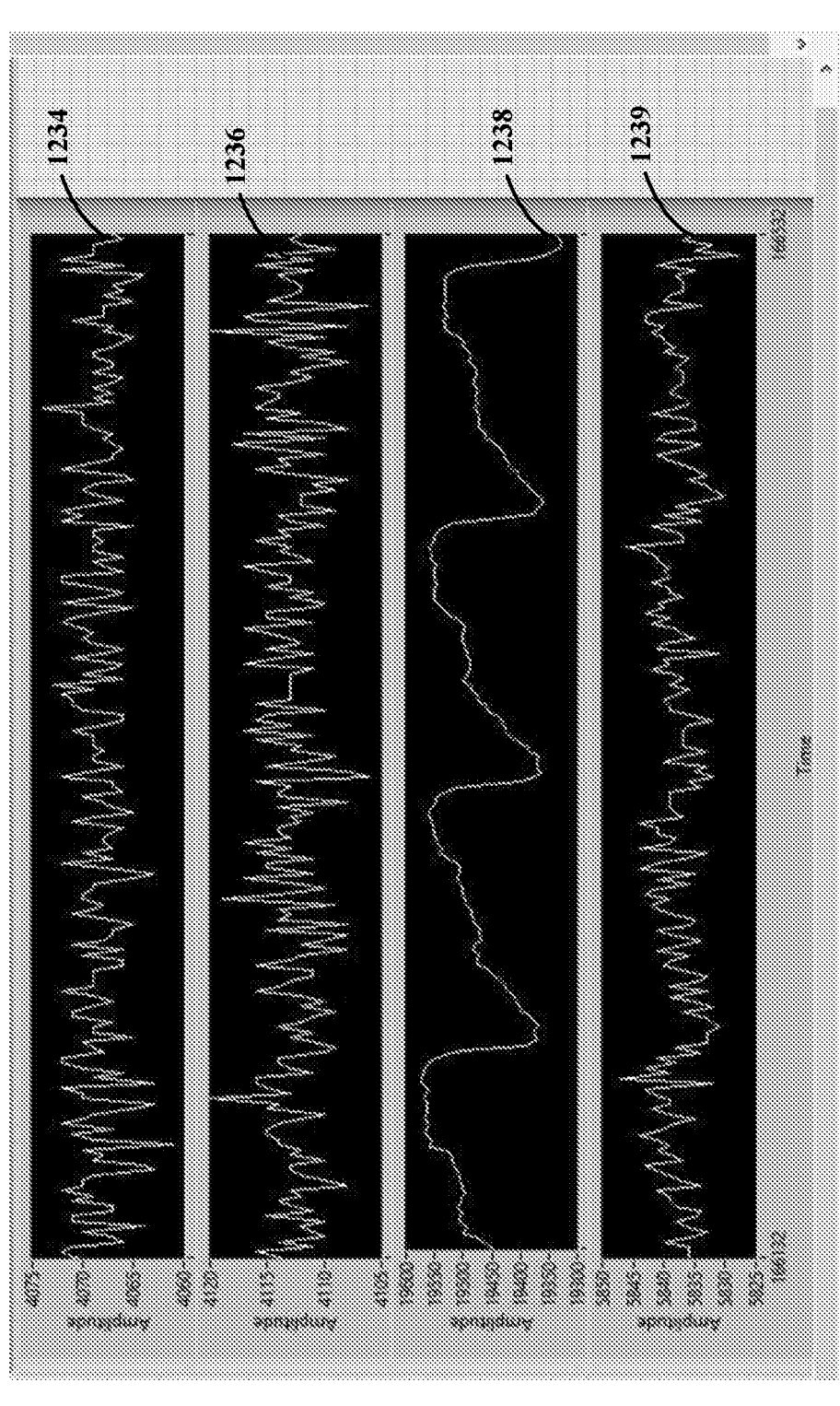
FIG. 12 illustrates example data captured using an apparatus, in accordance with the present disclosure.

FIG. 12 illustrates example data captured using an apparatus in accordance with various embodiments. As previously described, the apparatus includes at least one sensor circuit having an electrode, where the edge of the electrode is placed near the skin of the user. The edge contact can be near the skin but may not touch the skin of the user. The closer the edge contact is to the skin, the stronger the resulting signal is. FIG. 12 illustrates example pulse-waveform 1238 captured using the above-described apparatus. Pulse-waveform 1238 shows the signal from the sensor circuit and data 1234, 1236, and 1239 shows the signals from empty channels with no sensor circuits connected. In this example, the sensor circuit comprises a 6 mm wide copper tape electrode having an edge contact.

Figure 13A:
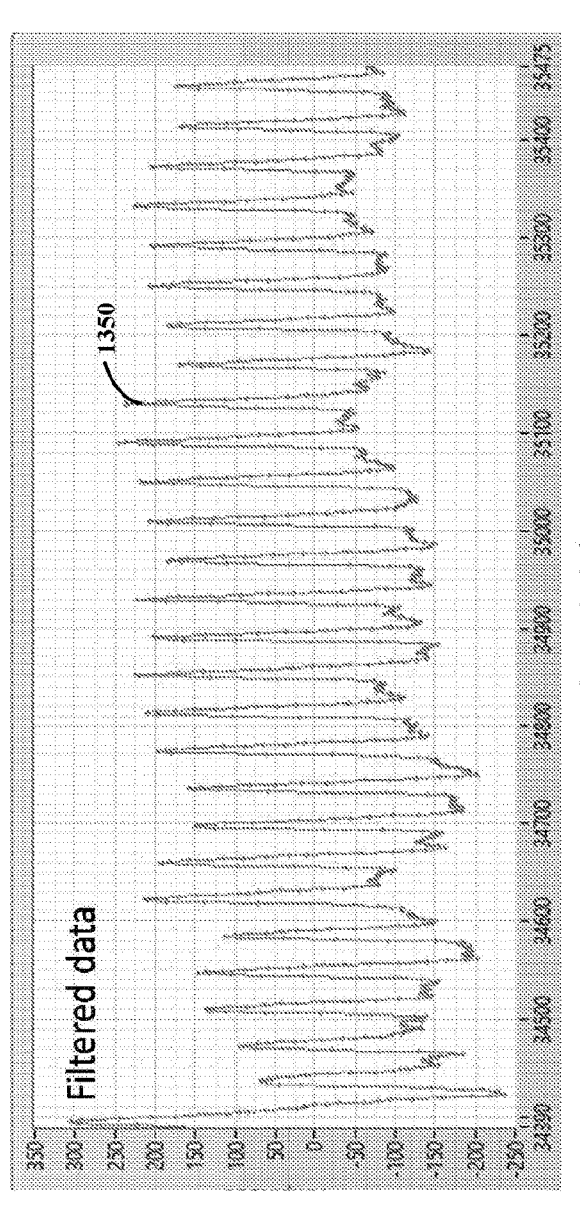
FIGS. 13A-13B illustrate example data captured using an apparatus, in accordance with the present disclosure.
Figure 13B:
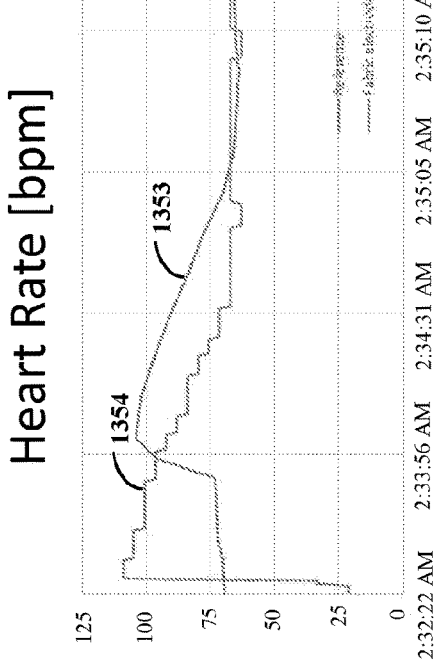

FIGS. 13A-13B illustrate example data captured using an apparatus in accordance with various embodiments. The apparatus includes a single electrode that is formed of conductive cloth. For example, the cloth electrode can be 2 mm wide and 2 cm long. FIG. 13A illustrates an example pulse-waveform 1350 captured using the cloth electrode. The electrode can lie flat on the skin of the user and can be held in place on the skin by a wristband. The user's arm can be bent with a hand elevated and the data is captured after the user has been running in place. FIG. 13B illustrates an example graph of a heartrate varying over time 1354 and as generated using the data illustrated by FIG. 13A. A bandpass filter (20 Hz/0.5 Hz) is used to process the pulse-waveform data, the heartrate is calculated from the Fourier transform of the pulse-waveform, and the heartrate value can be averaged over a period of time (e.g., 15 seconds). The reference data 1353 in this example lags the experimental data by a period of time (e.g., 30 seconds) due to differences in averaging periods.

Figure 14:
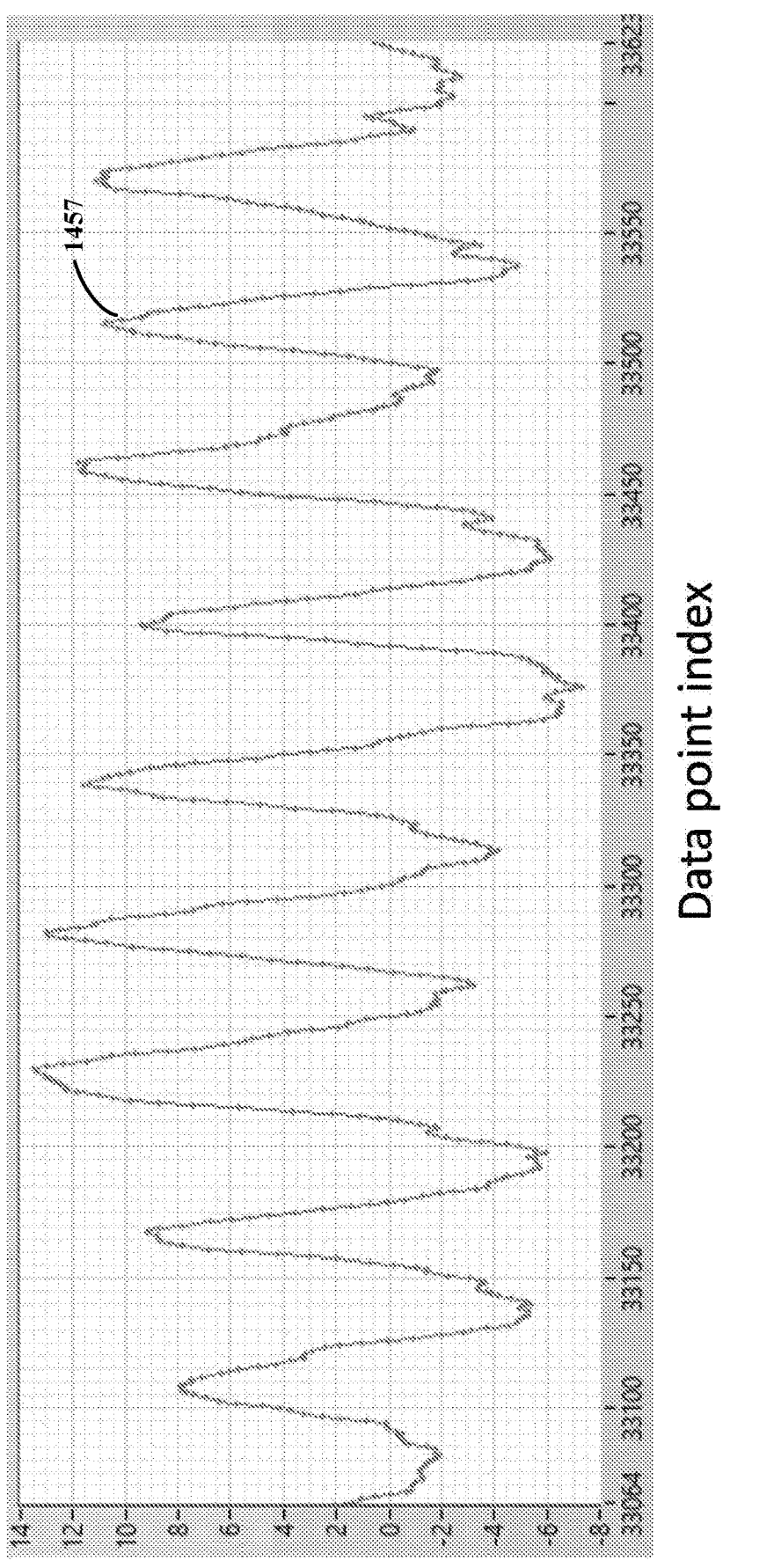
FIG. 14 illustrates example data captured using an apparatus, in accordance with the present disclosure.

FIG. 14 illustrates example data captured using an apparatus in accordance with various embodiments. The apparatus includes a single (braided) wire electrode. As illustrated, the data captured includes a pulse-waveform 1457. To determine a heartrate, a bandpass filter (1 Hz/2 Hz) is used to extract the heartrate data. In an example experimental embodiment, the calculated heartrate is 71 bpm, and the reference heartrate (Fitbit Charge HR™) is 72 bpm. The electrode can be formed of steel (e.g., steel picture wire) and held in place by an elastic wristband.

Figures 15A, 15B:
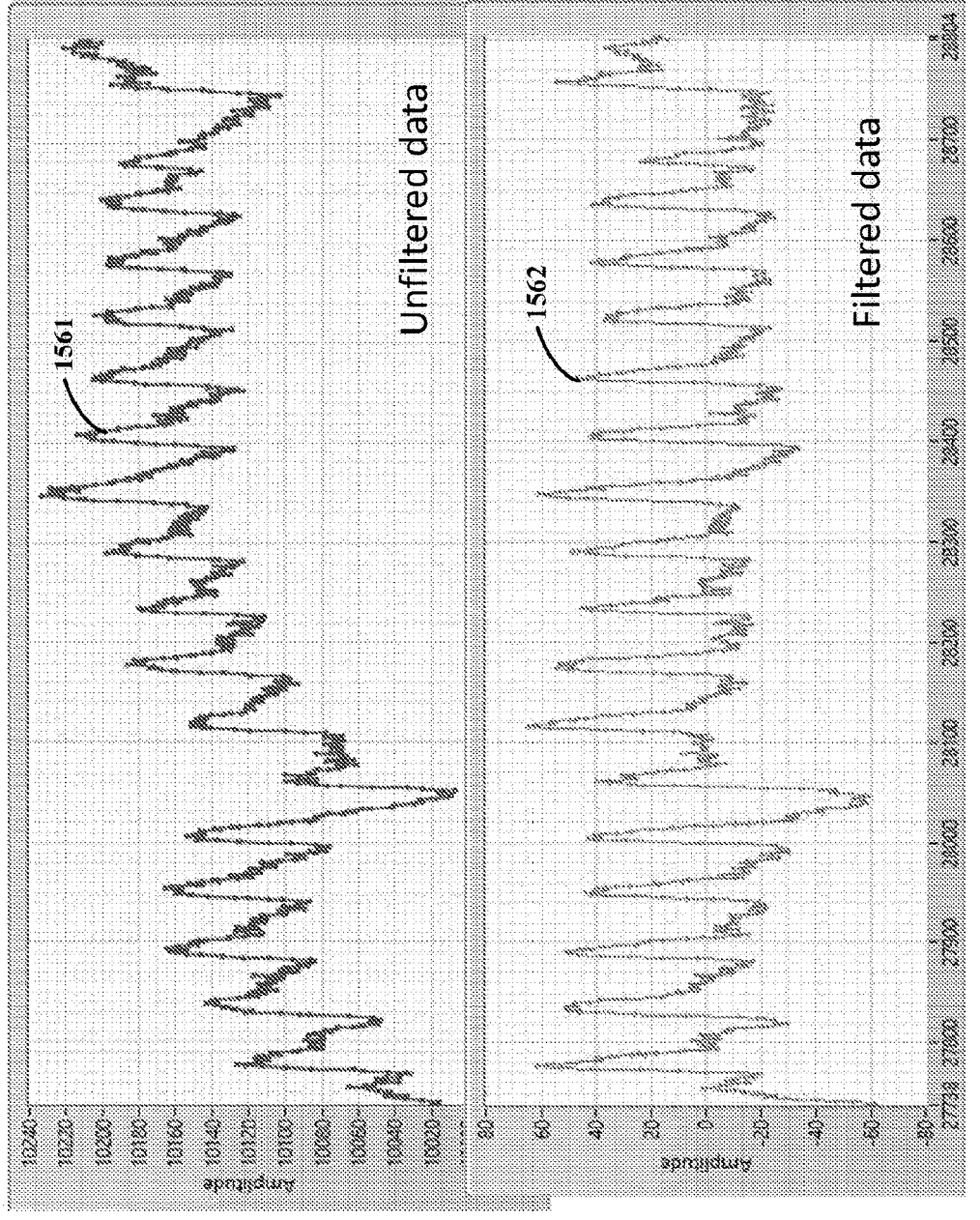
FIGS. 15A-15B illustrate an example apparatus and data captured using the apparatus, in accordance with the present disclosure.

FIGS. 15A-15B illustrate an example apparatus and data captured using the apparatus in accordance with various embodiments. As illustrated by FIG. 15A, the electrode 1559 can include more complex geometrics, such as a star shaped copper foil electrode that lies flat on the skin of the user and is held in place on the skin by a wristband. FIG. 15B illustrates an example pulse-waveform captured as filtered and unfiltered using the apparatus illustrated in FIG. 15A (e.g., the unfiltered waveform 1561 and filtered waveform 1562). A bandpass filter (20 Hz/0.5 Hz) is used to extract the data. In an example experimental embodiment, the calculated heartrate is 71 bpm, and the reference heartrate (Fitbit Charge HR™) is 71 bpm.

With reference to the block diagram illustrated by FIG. 3, signal flow from the body-wear transducer is processed by a signal converter for digital processing (at microcontroller) for wireless (and/or wired) communications to a remote user interface. In certain embodiments, the relevant signals are picked up by the sensor circuit and processed and detected/measured by the transducer (e.g., the capacitance-to-digital converter) and the electrical-signal sensing circuit (e.g., the microcontroller), independent of whether or not the transducer and/or the sensor circuit is initially configured to touch the user's skin (as in the case of an electrical-conducting transducer that relies purely on electrical conduction), and/or a specific type of interface between the user's skin and the transducer. Depending on the possible above-noted mechanism(s), contrary to conventional sensor approaches, such embodiments do not rely on the amount of initial contact with the user's skin and/or interface type (such conventional sensor approaches are insensitive to changes in fringe field and/or small changes in the distance between the electrode and the skin). In various embodiments, the signals carried by the electrode are not are influenced or altered by changes in brightness attributable to the hemodynamic or pulse-wave events, such as with a photoplethysmogram (PPG) sensor.

The sensor circuit including the single electrode in various embodiments is used to perform proximity sensing. As previously described, changes in capacitance are carried by the electrode and respective sensor circuit and are responsive to pressure and/or electric field modulations attributable to hemodynamic or pulse-wave events. The capacitance changes may be due to changes in the pressure, geometry, or electric field distribution of the blood vessels, but are such parameters are not directly measured. The sensor circuit and electrode captures (or senses) the capacitance changes through proximity sensing of the skin of the user (as opposed to physically deforming the device as a capacitance sensor), and thereby acts as or is a proximity sensor. The proximity sensing and/or capacitance changes are responsive to modulating distances between the skin of the user and the sensor circuit and/or modulating fringe field lines.

The various embodiments described above and as further described in the below more detailed/experimental embodiments, make reference to a user and the respective wearable apparatus confirming to the skin or body of the user. One of ordinary skill may appreciate that a user is not limited to a human. In accordance with specific embodiments, the user can include an organism or animal (other than a human), such as horses, dogs, cows, birds, reptiles, various animals being monitored in a zoo or other types of organism or animals (e.g., zebras, elephants, pandas, etc.), organism or animals being monitored in the wild, among other organisms. The user's (e.g., an animal) skin may be covered in hair and above-described wearable apparatus can conform to or be mechanically constrained to the body of the user (e.g., the animal).

Slides 17 and 18 of the underlying Provisional Application (Ser. No. 62/314,474), entitled "Proximity Sensors and Related Sensing Methods", filed Mar. 29, 2019, show, for certain specific exemplary embodiments, a detailed diagram showing an example of how such a sensor circuit can be implemented, which is incorporated herein in its entirety for its teachings.

MORE DETAILED/EXPERIMENTAL EMBODIMENTS

Embodiments in accordance with the present disclosure include use of an apparatus, which includes an electrical-signal sensing circuit and at least one sensor circuit having an electrode, to monitor capacitance changes and/or relative capacitance changes responsive to changes in the distance between a respective electrode and the skin of the user and/or changes in the electric field near an arterial pulse point caused by pulse-wave events. Using the changes in capacitance, a pulse-waveform and/or pressure differentials can be determined. The pulse-waveform can be used to determine various hemodynamic parameters and/or changes in the parameters including heart rate, diastolic blood pressure, systolic blood pressure, arterial stiffness, and blood volume in a non-invasive manner.

Figure 16:
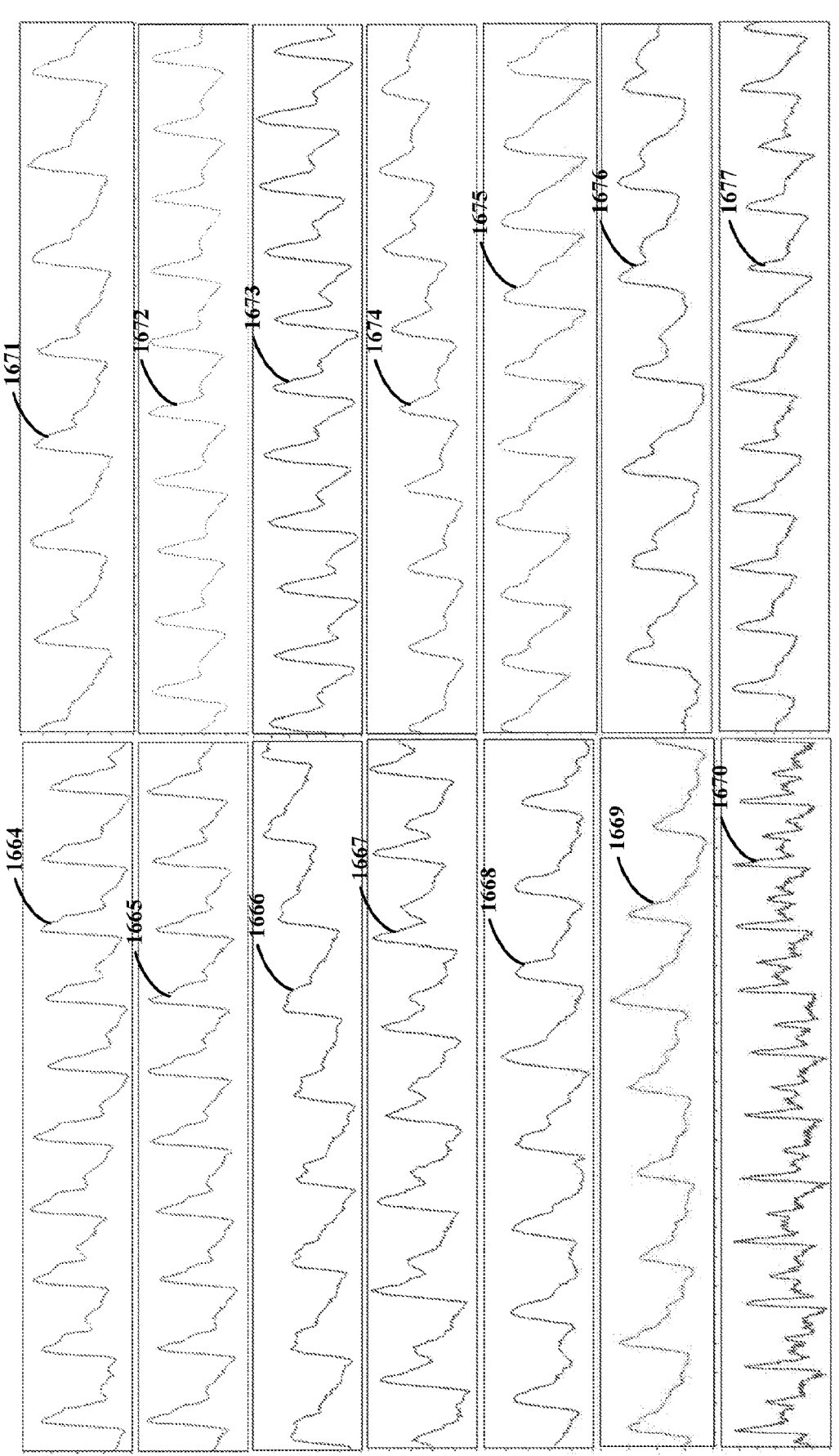
FIG. 16 illustrates examples of data collected using an apparatus, in accordance with the present disclosure.

FIG. 16 illustrates example data collected using an apparatus, in accordance with various embodiments. The data includes a range of different shaped pulse-waveforms 1664, 1665, 1666, 1667, 1668, 1669, 1670, 1671, 1672, 1673, 1674, 1675, 1676, and 1677 (herein generally referred to as the "pulse-waveforms" for ease of reference) that can be captured using an apparatus in accordance with the present disclosure. The illustrated pulse-waveforms are obtained by measuring the relative changes in capacitance, and not based on absolute value in capacitance. However embodiments in accordance with the present disclosure are not so limited.

Figures 17A, 17B, 17C:
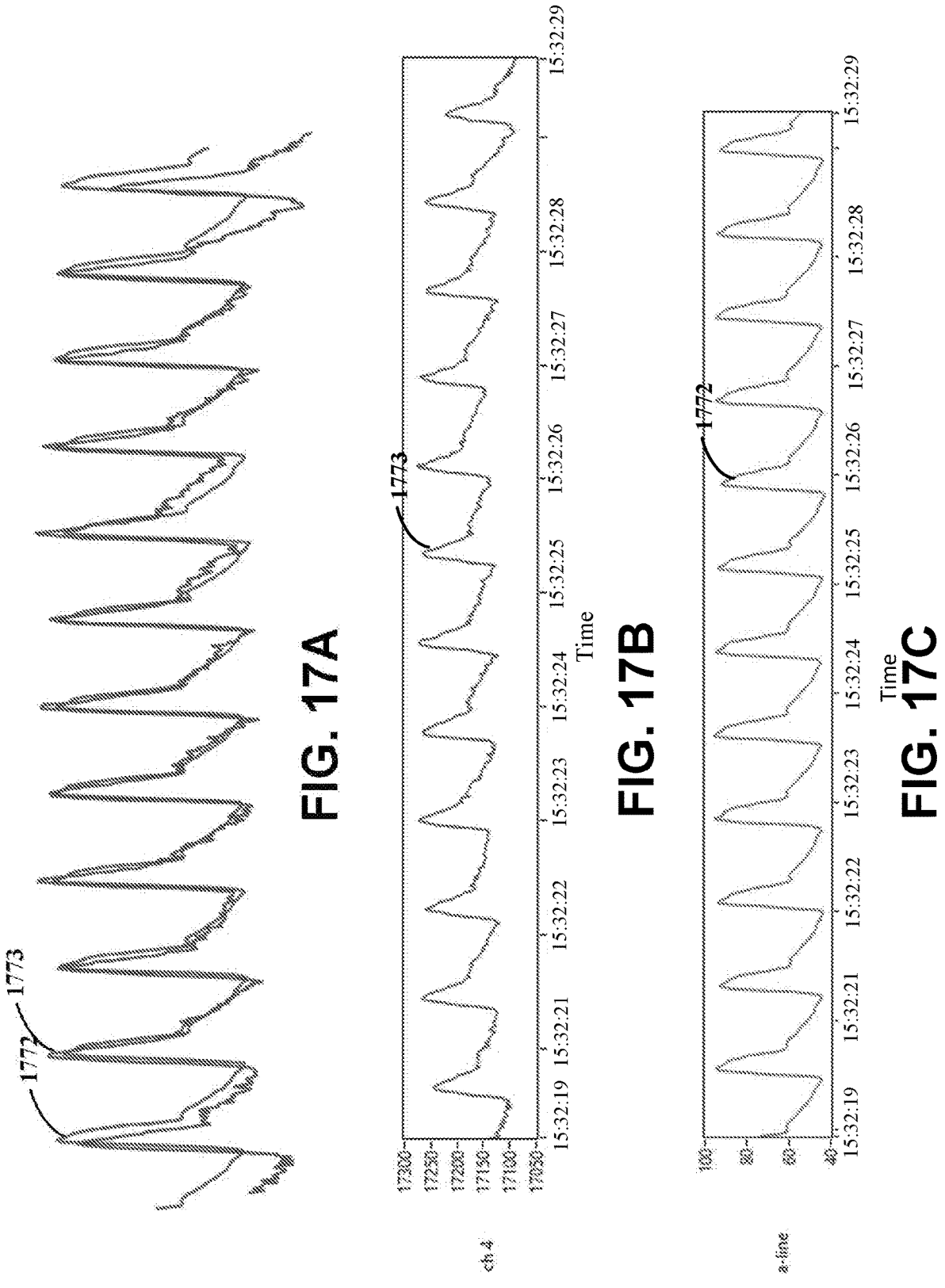
FIGS. 17A-17C illustrate example data collected using an apparatus and data collected using an arterial line, in accordance with various experimental embodiments.

FIGS. 17A-17C illustrate example data collected using an apparatus and data collected using an arterial line, in accordance with various experimental embodiments. The data obtained using an apparatus (that is placed proximal to the left radial pulse point of a user) tracks and/or mimics data obtained using an arterial line implanted in the right radial artery. FIG. 17A illustrates that the data 1773 obtained by apparatus in accordance with various embodiments mimics the data 1772 obtained by the arterial line. FIG. 17B illustrates the data 1773 (e.g., the waveform) and FIG. 17C illustrates the data 1772, separately for further illustration.

Figures 18A, 18B, 18C:
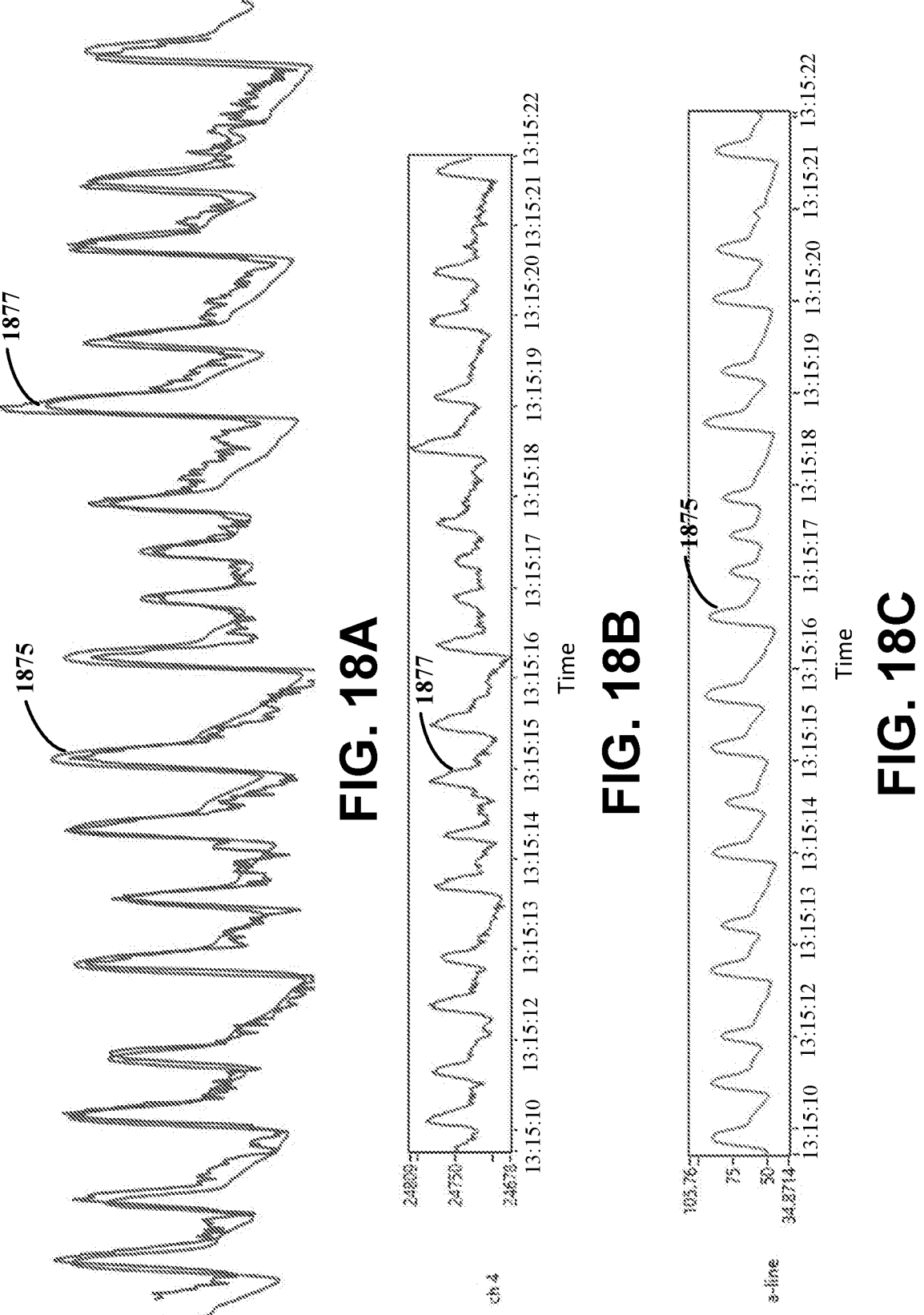
FIGS. 18A-18C illustrate example data collected using an apparatus and collected using an arterial line, in accordance with various experimental embodiments.

FIGS. 18A-18C illustrate example pulse-waveform data collected using an apparatus and collected using an arterial line, in accordance with various experimental embodiments. The data obtained using an apparatus (that is placed proximal to the left radial pulse point of a user) tracks and/or mimics data obtained using an arterial line implanted in the right radial artery. The heartrate can be determined on a beat-by-beat analysis by measuring the length of the pulse. The heartrate variability can be determined from the distribution of individual heartrate values. FIG. 18A illustrates that the pulse-waveform data 1877 obtained by apparatus can mimic the pulse-waveform data 1875 obtained by the arterial line. FIG. 18B illustrates the pulse-waveform data 1877 (e.g., the waveform) and FIG. 18C illustrates the pulse-waveform data 1875, separately for further illustration.

Figures 19A, 19B, 19C:
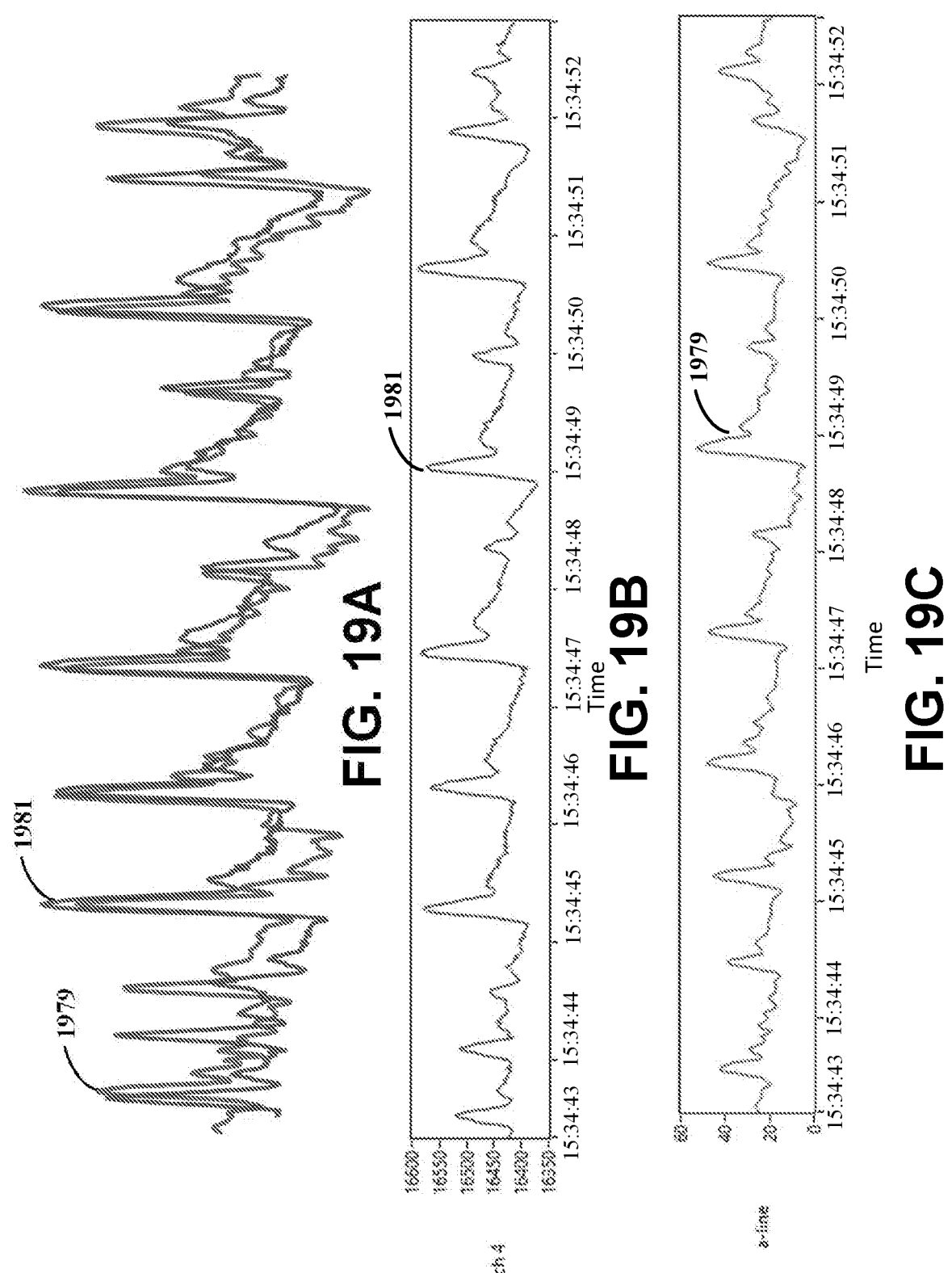
FIGS. 19A-19C illustrate an example of changes in heart rate and blood pressure as collected using an apparatus and collected using an arterial line, in accordance with various experimental embodiments.

FIGS. 19A-19C illustrate example of changes in heartrate and blood pressure as collected using an apparatus and collected using an arterial line, in accordance with various experimental embodiments. Patterns and anomalies in heartrate and blood pressure can be tracked and/or monitored, in various embodiments. Such patterns and/or anomalies can be indicative of various health conditions, such as atrial fibrillation, hypertension, peripheral vascular disease, aortic regurgitation, aortic stenosis, and/or left ventricular obstruction, among other conditions. The data obtained using an apparatus (that is placed proximal to the left pulse point of a user) can track and/or mimic data obtained using an arterial line implanted on the right radial artery. FIG. 19A illustrates that the data 1981 obtained by apparatus in accordance with various embodiments mimics the data 1979 obtained by the arterial line. FIG. 19B illustrates the data 1981 (e.g., the waveform) and FIG. 19C illustrates the data 1979, separately for further illustration.

Figure 20:
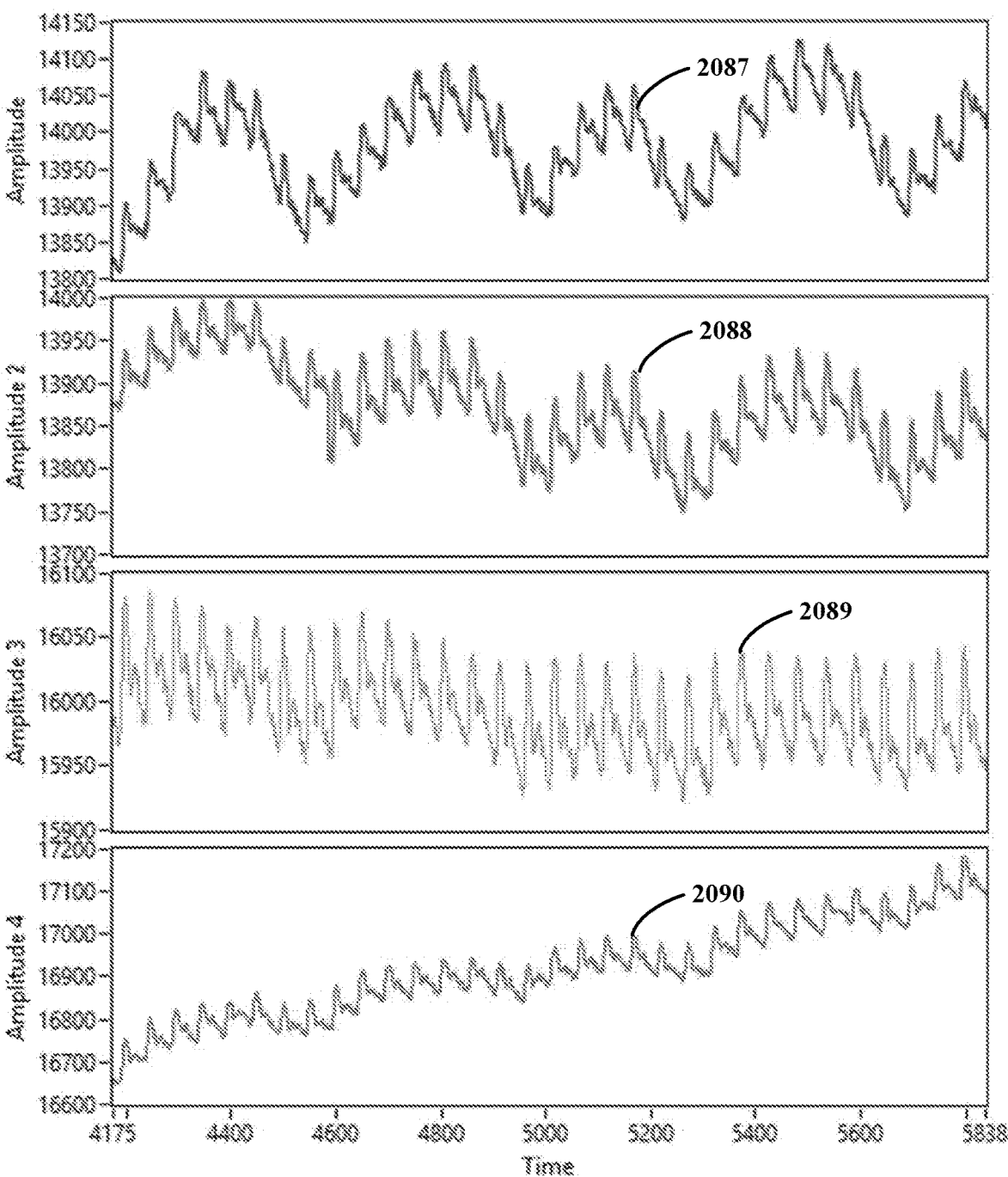
FIG. 20 illustrate example respiration rates collected using an apparatus in accordance with various experimental embodiments.

FIG. 20 illustrates example respiration rates collected using an apparatus in accordance with various experimental embodiments. The apparatus can be used to measure and/or monitor respiration rates from breathing modes. For example, FIG. 20 illustrates data 2087, 2088, 2089, 2090 captured using four different channels and showing a periodic baseline shift with a characteristic frequency related to the breathing motion of the user.

Figure 21:
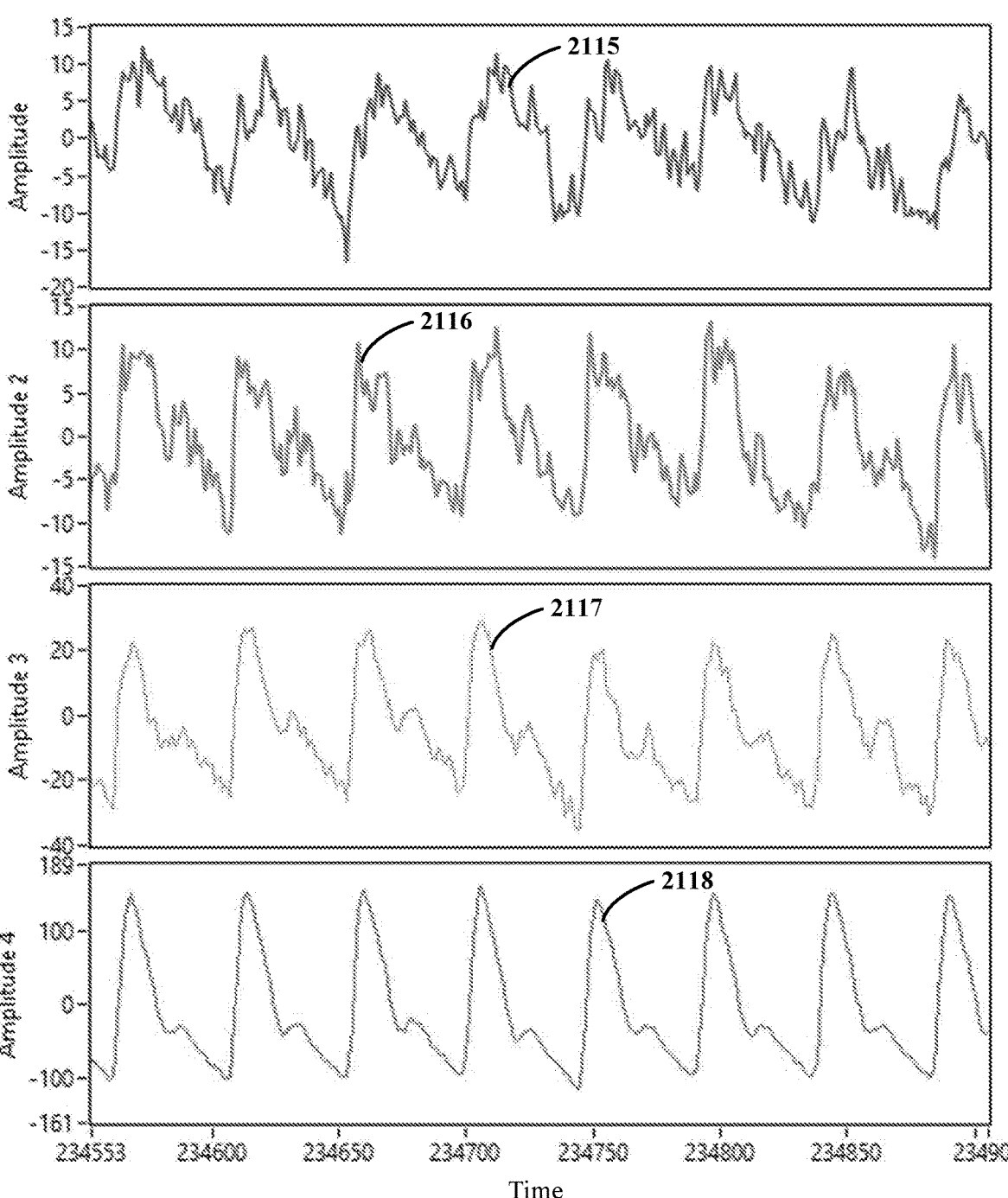
FIG. 21 illustrates example data collected using an apparatus having multiple electrodes in accordance with various experimental embodiments.

FIG. 21 illustrates example data collected using an apparatus having multiple electrodes located at different positions in accordance with various experimental embodiments. The electrodes, as previously described, can be arranged to have multiple channels respectively carrying signals for processing by the electrical-signal sensing circuit. The quality and amplitude of the data captured between channels (that can be simultaneously captured) can vary due to the respective position of each electrode. FIG. 21 illustrates filtered data 2115, 2116, 2117, 2118 (e.g., raw data that is filtered captured using the four channels).

Figure 22:
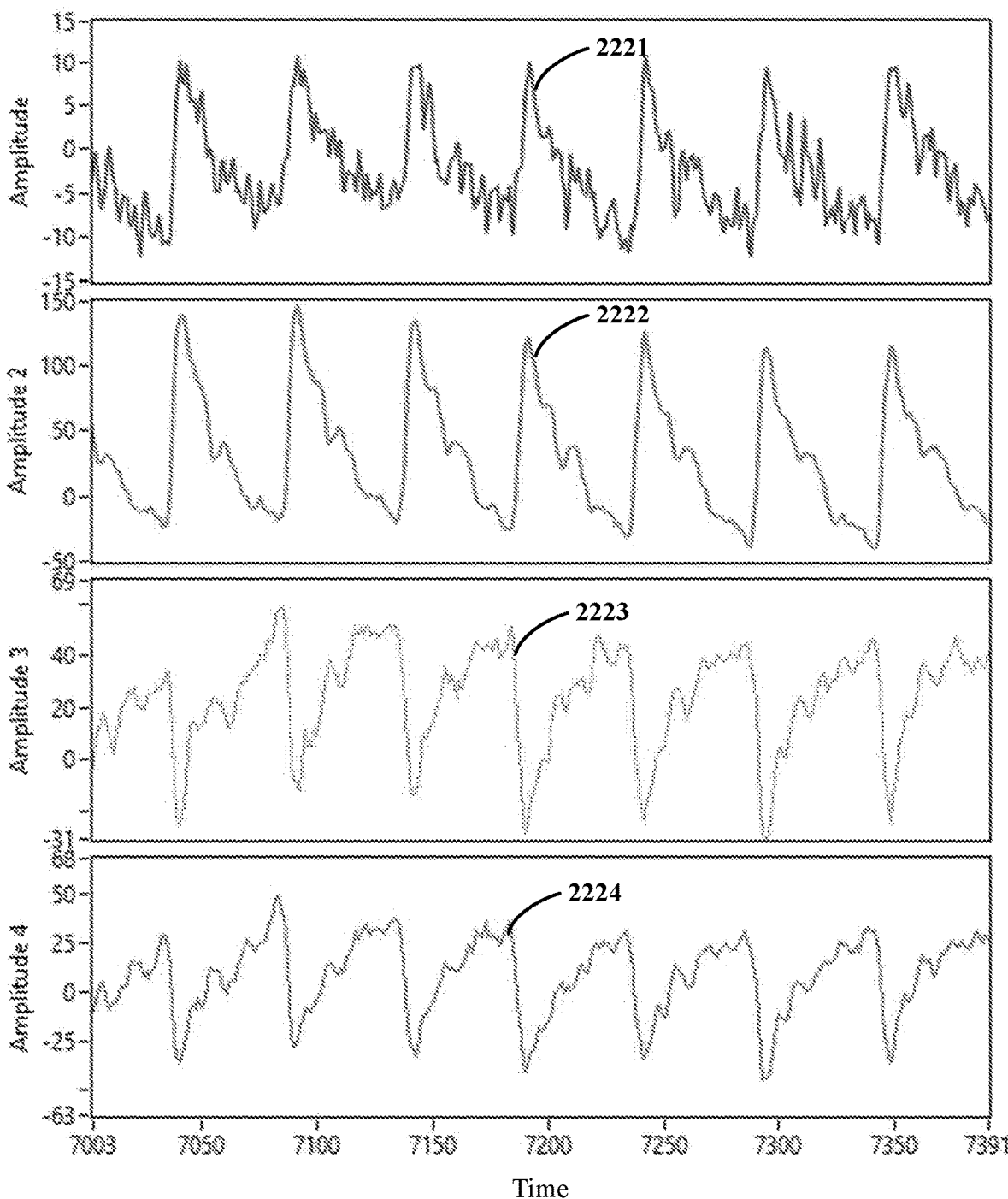
FIG. 22 illustrates example data collected using an apparatus having multiple electrodes located at different positions in accordance with various experimental embodiments.

FIG. 22 illustrates example data collected using an apparatus having multiple electrodes located at different positions in accordance with various experimental embodiments. The position of the electrodes, as previous discussed above with respect to FIG. 21, can impact the quality of the data captured. In addition and/or alternatively, the position of the electrodes can result in a mixture that is (respectively) normal and inverted. FIG. 22 illustrates the filtered data 2221, 2222, 2223, 2224 captured using the four channels, as previously described.

Figure 23:
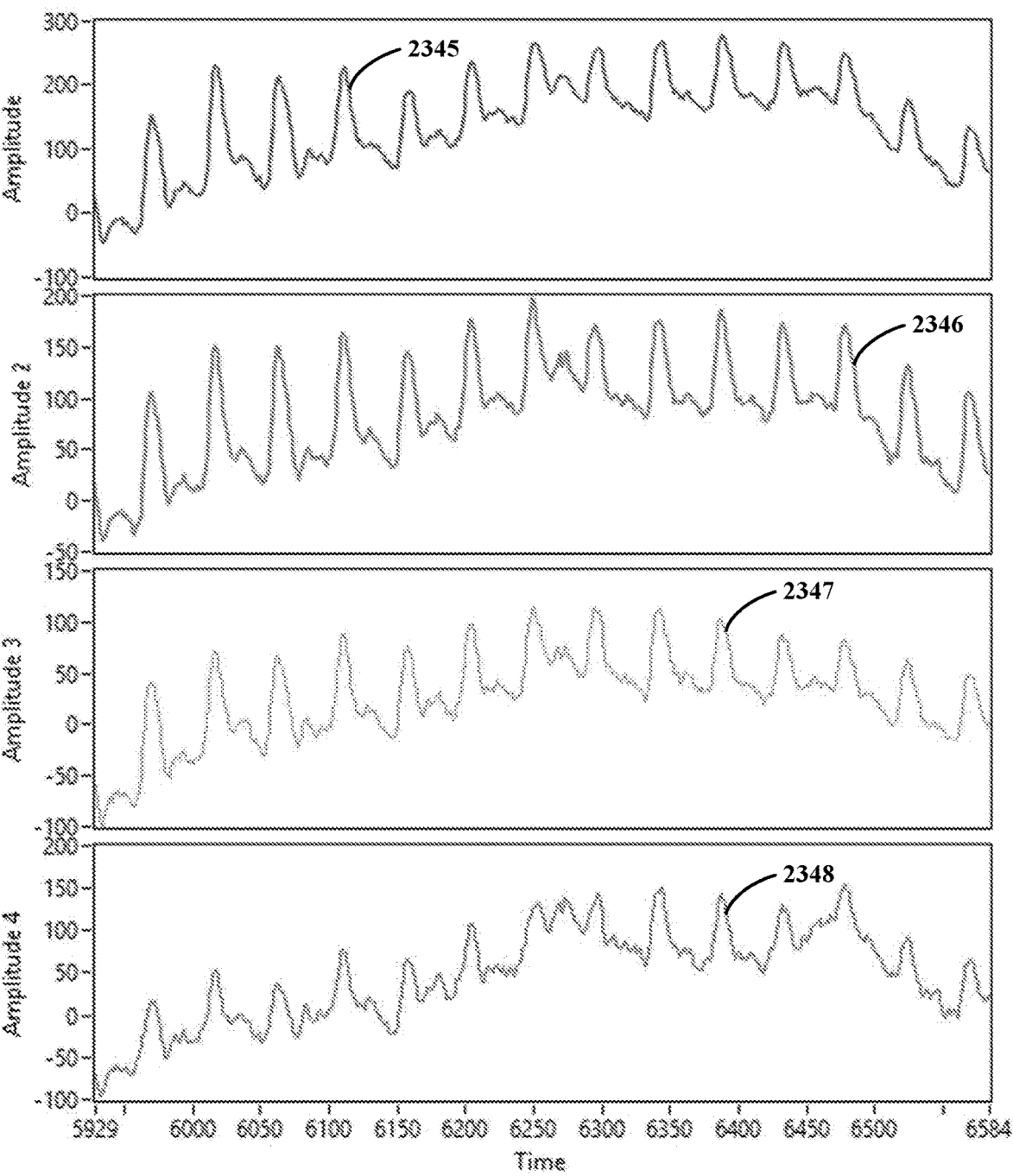
FIG. 23 illustrates example data collected using an apparatus having multiple electrodes in accordance with various experimental embodiments.

FIG. 23 illustrates example data collected using an apparatus having multiple electrodes in accordance with various experimental embodiments. In various embodiments, the data captured using the electrode(s) can be processed to decrease baseline drift and signal noise using a bandpass filter. For example, FIG. 23 illustrates the filtered data 2345, 2346, 2347, 2348 captured using the same four channels (e.g., as filtered using a 0.1 to 20 Hz bandpass filter).

As illustrated and previously described, the pulse-waveform can be used to determine various hemodynamic parameters. For example, the shape and other features of the pulse-waveform can be correlated to blood pressure. In other embodiments, the heart rate and heart variability can be obtained by determining the timings of each pulse. Further, the changes in blood pressure can be monitored by first calibrating the data (such as with arterial lines that are calibrated against inflatable cuff data).

Various different techniques can be used to analyze the pulse-waveform and/or to determine various hemodynamic parameters including feature analysis and computation fluid dynamics techniques. For example, features attributed to hemodynamic phenomena can be correlated to blood pressure, arterial stiffness, and other hemodynamic parameters. For more general and specific information on features attributed to hemodynamic phenomena, reference is made to Cecelia, Marina, and Phil Chowienczyk. "Role of Arterial Stiffness in Cardiovascular Disease." JRSM Cardiovascular Disease 1.4 (2012): cvd.2012.012016, PMC, Web. 31 Jan. 2017; David A. Donley et al, "Aerobic exercise training reduces arterial stiffness in metabolic syndrome" Journal of Applied Physiology published 1 Jun. 2014, Vol 116, no. 11, 1396-1404; Baruch, Martin C. et al. "Validation of the pulse decomposition analysis algorithm using central arterial blood pressure." *Biomedical engineering online* 13.1 (2014): 96, and Munir, Shahzad, et al. "Peripheral augmentation index defines the relationship between central and peripheral pulse pressure," *Hypertension* 51.1 (2008): 112-118, each of which are fully incorporated herein. As another example, the augmentation index (AI), (peripheral second systolic blood pressure (pSBP$_2$)–diastolic blood pressure (DBP))/(peripheral systolic blood pressure (pSBP)–DBP) can be used as a marker for arterial stiffness and may be correlated to both peripheral and central peak blood pressure (pPP & cPP). AI is a normalized parameter and can be analyzed without absolute calibration. Computation fluid dynamic techniques can include modeling vasculature as an inductor capacitor resistor (LCR) circuit and/or as a network of elastic pipes to calculated parameters such as pulse-wave velocity and/or waveform shape. For more general and specific information related to computation fluid dynamics used to determine hemodynamic parameters, reference is made to Lee, Byoung-Kwon. "Computational fluid dynamics in cardiovascular disease," *Korean circulation journal*

41.8 (2011): 423-430, and Xiaoman Xing and Mingshan Sun, "Optical blood pressure estimation with photoplethysmography and FFT-based neural networks," Biomed. Opt. Express 7, 3007-3020 (2016), each of which are fully incorporated herein. One model that can be used to derive a relationship between the pulse-waveform (obtained by PPG) and blood pressure, where g is defined by the modulus E of the blood vessel walls, includes:

$$E=E_0 e^{\gamma P}.$$

For example, a normalized waveform can be given by:

$$= \frac{V - V_{min}}{V_{min}},$$

$$\frac{2(e^{-\gamma P_{min}} - e^{\gamma P})}{b - 2e^{-\gamma P_{min}}},$$

$$\propto k(e^{-\gamma P_{min}} - e^{-\gamma P}.$$

Various techniques can be used for correlating the pulse-waveform to blood pressure values. For more general and specific information related to correlating pulse-waveforms to blood pressure values, reference is made to Xing, Xiaoman, and Mingshan Sun. "Optical Blood Pressure Estimation with Photoplethysmography and FFT-Based Neural Networks." *Biomedical Optics Express* 7.8 (2016): 3007-3020, and http://cs229.stanford.edu/proj2014/Sharath%20Ananth, Blood%20Pressure%20Detection%20from%20PPG.pdf, each of which are fully incorporated herein.

Figure 24A:
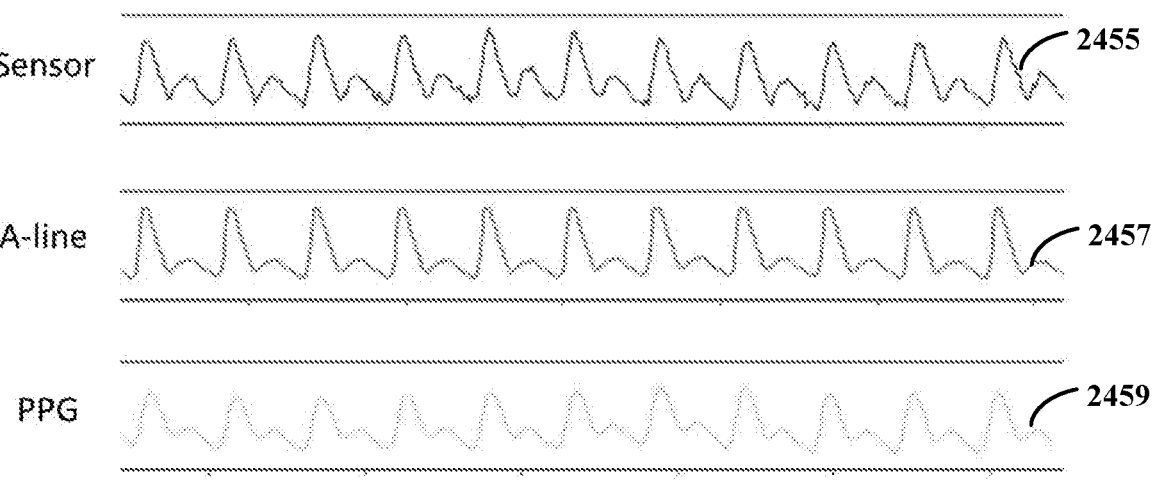
FIGS. 24A-24B illustrate example pulse-waveforms generated using a wearable apparatus, an arterial line, and an optical sensor, in accordance with various embodiments.
Figure 24B:
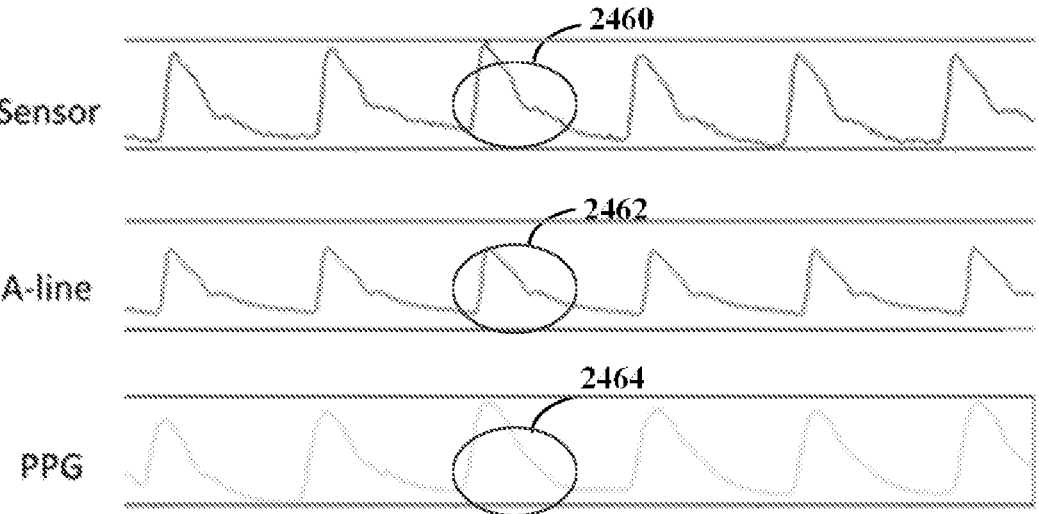

FIGS. 24A-24B illustrate example pulse-waveforms generated using a wearable apparatus, an arterial line, and an optical sensor, in accordance with various embodiments. The wearable apparatus includes sensor circuit having the electrode, as previously described.

As illustrated by FIG. 24A, the pulse-waveform 2455 generated using the wearable apparatus captured secondary features, particularly when the secondary features are large and separated from the primary peak. Further, the pulse-waveform 2455 resembles the pulse-waveform 2457 generated using the arterial line and the pulse-waveform 2459 generated using the optical sensor (e.g., the photoplethysmogram (PPG)).

FIG. 24B illustrates the ability of the electrical-signal sensing apparatus to capture subtle features of the pulse-waveform 2460 that can correlate the waveform to blood pressure. Such features, which are highlighted by the circle around portions of the pulse-waveforms 2460, 2462, 2464, can be washed out with PPG sensors as illustrated by the pulse-waveform 2464 captured using a PPG.

Terms to exemplify orientation and direction, such as upper/lower, left/right, top/bottom, up/down, above/below, vertical, horizontal, and perpendicular, may be used herein to refer to relative positions of elements as shown in the figures. Similarly, as heating and cooling are relative terms of art, it is appreciated that a heating source and a cooling source can be synonymous considering that the direction of temperature change can be controlled according to the desired temperature change. It should be understood that the terminology is used for notational convenience only and that in actual use the disclosed structures may be oriented different from the orientation shown in the figures. Thus, the terms should not be construed in a limiting manner.

It may also be helpful to appreciate the context/meaning of the following terms: the term "electrode" refers to or includes a conductive conductor; the term "sensor circuit"

refers to or includes to a circuit including the electrode and a connection to the transducer circuit (e.g., has a sensor connector for the electrode to be plug in or otherwise connected to the transducer circuit), and that detects or measures the capacitance values and/or changes in capacitance via the electrode and is used to output the same to the transducer circuit; the sensor circuit may additionally include various other elements, such as those illustrated by FIGS. 4A-4B and 5A-5B, for example, the sensor circuit can include a multilayer construction that includes the electrode and various dielectric and conductive layers; the term "transducer circuit" refers to or includes circuitry that converts variations in a physical quality, such as changes in capacitance as provided by the sensor circuit, into electrical signals; for example, the transducer circuit can include a capacitance-to-digital converter; the term "pulse-wave events" refers to or includes hemodynamic responses and/or attributes caused by and/or indicative of heart beats (e.g., contraction of heart muscles) (e.g., heart beats or sounds, changes in blood pressure or blood flow velocity, etc.); the term "pulse-waveform" refers to or includes a signal or wave shape generated by the pulse-wave events; example pulse-waveforms include an arterial pulse waveform, e.g., a wave shape generated by the heart when the heart contracts and the wave travels along the arterial walls of the arterial tree; the term "electrical-signal sensing circuit" refers to or includes a circuit that is used to sense the hemodynamic or pulse-wave events using the electrical signals from the transducer circuit; an example electrical-signal sensing circuit includes a microcontroller or other processing circuitry and an example transducer circuit includes a capacitance-to-digital converter, although embodiments are not so limited; the term "communication circuit" refers to or includes a circuit that outputs data to other external circuitry, which can include a wireless or a wired communication; an example communication circuit includes a transceiver, although embodiments are not so limited; the terms "hemo-dynamic" or "hemodynamic parameters" refers to or includes parameters relating to the flow of blood within the organs, blood vessels, and tissues of the body; example hemodynamic or hemodynamic parameters can include diastolic blood pressure, systolic blood pressure, arterial stiffness, and blood volume, among other parameters.

Various embodiments are implemented in accordance with the underlying Provisional Application (Ser. No. 62/314,474), entitled "Proximity Sensors and Related Sensing Methods", filed Mar. 29, 2016, to which benefit is claimed and which are fully incorporated herein by reference. For instance, embodiments herein and/or in the provisional application (including the slides therein) may be combined in varying degrees (including wholly). Reference may also be made to the experimental teachings and underlying references provided in the underlying provisional application, including the slides that form part of the provisional application. Embodiments discussed in the slides are not intended, in any way, to be limiting to the overall technical disclosure, or to any part of the claimed invention unless specifically noted.

Various blocks, modules or other circuits may be implemented to carry out one or more of the operations and activities described herein and/or shown in the figures. For example, processes such as heating, etching, and deposition can be automated through the use of various circuits and associated machines. In these contexts, various depicted functions can be implemented using a circuit that carries out one or more of these or related operations/activities. In various embodiments, a hard-wired control block can be used to minimize the area for such an implementation in case a limited flexibility is sufficient. Alternatively and/or in addition, in certain of the above-discussed embodiments, one or more modules are discrete logic circuits or programmable logic circuits configured and arranged for implementing these operations/activities.

As examples, the Specification describes and/or illustrates aspects useful for implementing the claimed disclosure by way of various circuits or circuitry which may be illustrated as or using terms such as blocks, modules, device, system, and/or other circuit-type depictions. Such circuits or circuitry are used together with other elements (wristbands, external processing circuitry and the like) to exemplify how certain embodiments may be carried out in the form or structures, steps, functions, operations, activities, etc. For example, in certain of the above-discussed embodiments, one or more illustrated items in this context represent circuits (e.g., discrete logic circuitry or (semi-)programmable circuits) configured and arranged for implementing these operations/activities, as may be carried out in the approaches shown in the slides. In certain embodiments, such illustrated items represent one or more computer circuitry (e.g., microcomputer or other CPU) which is understood to include memory circuitry that stores code (program to be executed as a set/sets of instructions) for performing a basic algorithm (e.g., monitoring pressure differentials and/or capacitance changes attributable to pulse-wave events), and/or involving determining hemodynamic parameters, and/or a more complex process/algorithm as would be appreciated from known literature describing such specific-parameter sensing. Such processes/algorithms would be specifically implemented to perform the related steps, functions, operations, activities, as appropriate for the specific application. The specification may also make reference to an adjective that does not connote any attribute of the structure ("first [type of structure]" and "second [type of structure]") in which case the adjective is merely used for English-language antecedence to differentiate one such similarly-named structure from another similarly-named structure (e.g., "first electrode . . . " is interpreted as "an electrode . . . ").

Based upon the above discussion and illustrations, those skilled in the art will readily recognize that various modifications and changes may be made to the various embodiments without strictly following the exemplary embodiments and applications illustrated and described herein. For example, methods as exemplified in the Figures may involve steps carried out in various orders, with one or more aspects of the embodiments herein retained, or may involve fewer or more steps. Such modifications do not depart from the true spirit and scope of various aspects of the disclosure, including aspects set forth in the claims

What is claimed is:

1. A wearable apparatus comprising:
a transducer circuit including a sensor circuit to sense changes in capacitance through a user's skin without relying on an active portion of the sensor circuit being in contact with the user's skin where the changes are to be sensed and being configured to convert the changes in capacitance into electrical signals;
a layered portion, as part of the sensor circuit, including a dielectric layer adjacent to or stacked with a conductive electrode layer and including one or more spacers to control or set a distance between the active portion of the sensor circuit and skin of the user, the changes in capacitance being responsive to at least one of pressure and electric field modulations attributable to hemodynamic or pulse-wave events of an arterial pulse wave-form manifesting primary peaks as pulse-waveform maxima and minima and manifesting one or more subtle features separated from the primary peaks and in between the pulse-waveform maxima and minima;

an electrical-signal sensing circuit to sense the primary peaks as pulse-waveform maxima and minima and to sense the one or more subtle features separated from the primary peaks and in between the pulse-waveform maxima and minima in response to the electrical signals from the transducer circuit;

a substrate to support and at least partially enclose the transducer circuit and the electrical-signal sensing circuit, and to conform to a portion of the user and position the conductive electrode layer sufficiently close to the user's skin to facilitate the sensor circuit sensing the changes in capacitance; and a communication circuit to respond to the electrical-signal sensing circuit by conveying data, indicative of the one or more subtle features.

2. The wearable apparatus of claim 1, wherein the transducer circuit further includes a plurality of sensor circuits and a plurality of respectively-corresponding conductive electrode layers, each of the sensor circuits including only one conductive electrode layer, wherein the pressure change is indicative of the capacitance change.

3. The wearable apparatus of claim 1, wherein the sensor circuit is to capture the capacitance change through proximity sensing of the skin of the user in response to at least one of:

modulating distances between the user's skin and the sensor circuit; and modulating fringe field lines.

4. The wearable apparatus of claim 3, wherein the communication circuit is further to communicate the captured capacitance changes attributable to the hemodynamic or pulse-wave events to external processing circuitry.

5. The wearable apparatus of claim 1, wherein the transducer circuit is to be operated using a floating ground while the user wears the wearable apparatus on a portion of the user's body detached from any wires between the user's body and other electrical or electronics circuitry that is not coupled to the user's body and not part of the wearable apparatus and while the changes in capacitance are being sensed, and wherein the data indicative of the hemodynamic monitoring is also indicative of changes in at least one of the following: diastolic blood pressure, systolic blood pressure, and arterial stiffness.

6. The wearable apparatus of claim 1, wherein sufficiently close to the user's skin corresponds to the distance, while the user wears the wearable apparatus on a portion of the user's body detached from any wires between the user's body and other electrical or electronics circuitry that is not coupled to the user's body and not part of the wearable apparatus, relative to the portion of the user's body, wherein the distance is at most 1 millimeter (mm) away from the skin.

7. The wearable apparatus of claim 1, wherein comprising:

the transducer circuit has an array of electrical-signal sensing circuits, each of which is to sense and convert changes in capacitance into electrical signals, the changes in capacitance being responsive to at least one of pressure and electric field modulations attributable to hemodynamic or pulse-wave events sensed through the user's skin, without relying on the active portion of the electrical-signal sensing circuits being in contact with the user's skin where the changes are to be sensed;

and the communication circuit is to respond to the array of electrical-signal sensing circuits by sending data indicative of the hemodynamic monitoring, wherein different ones of the electrical-signal sensing circuits have different respective sensitivity levels.

8. The wearable apparatus of claim 7, wherein the transducer circuit includes an electrical-signal sensing circuit having only a single conductive electrode layer and being configured to monitor relative capacitance changes in a range of plus and minus 15 picofarad (pF) from a base capacitance of the electrical-signal sensing circuit.

9. The wearable apparatus of claim 1, further including at least two electrical-signal sensing circuits, wherein each of the electrical-signal sensing circuits includes a respective layered portion having a dielectric layer adjacent to or stacked with a conductive electrode layer, and the electrical-signal sensing circuits are cooperatively configured to provide a differential mode realized by subtracting out artifacts in response to the hemodynamic monitoring.

10. The wearable apparatus of claim 9, wherein the respective conductive electrode layers of the at least two electrical-signal sensing circuits are respectively associated with different characteristics based on at least one of electrode geometry and dielectric layers used with an associated one of the at least two electrical-signal sensing circuits.

11. The wearable apparatus of claim 10, wherein the at least two electrical-signal sensing circuits have encapsulants to set a sensitivity level.

12. The wearable apparatus of claim 1, further including a passively or inductively powered circuit to provide power to at least the electrical-signal sensing circuit.

13. The wearable apparatus of claim 1, wherein a portion of the dielectric layer encapsulates the layered portion.

14. The wearable apparatus of claim 1, wherein the substrate and the layered portion are configured as part of a user accessory and further configured to be sufficiently flexible for conforming to a wrist of or other body portion of the user.

15. The wearable apparatus of claim 1, wherein the sensor circuit includes a substrate portion that is to be mechanically constrained to the user's skin or another portion of the user's body with an adhesive applied to a perimeter region of the substrate portion, and the communication circuit is to send data, indicative of the one or more subtle features separated from the primary peaks and in between the pulse-waveform maxima and minima, to an external circuit that includes at least one of a display and a data-processor.

16. The wearable apparatus of claim 1, wherein the electrical-signal sensing circuit is further to determine hemodynamic parameters of the user or the user's heart using the hemodynamic or pulse-wave events.

17. The wearable apparatus of claim 1, wherein the substrate is characterized as being non-conductive and is configured to be worn on a wrist by being at least one of flexible and bendable, for conformance around the wrist.

18. The wearable apparatus of claim 1, wherein the layered portion is characterized in terms of thickness and flexibility for the sensor circuit to capture the hemodynamic or pulse-wave events in response to the electrical signals via at least one of a: pressure change in a range from 0.3 kilopascal to 1 kilopascal, and a capacitance change in a range defined as plus and minus 15 picofarads.

19. A method for hemodynamic monitoring via a wearable apparatus, the method comprising:

using a flexible or bendable substrate to secure a transducer circuit having at least one sensor circuit to sense changes in capacitance sensed through a user without relying on an active portion of the at least one sensor circuit being in contact with the user where the changes are to be sensed, the at least one sensor circuit including an electrical-signal sensing circuit and including a layered portion, wherein the layered portion includes at least one conductive electrode layer and at least one other different material layer and includes one or more spacers to control or set a distance between the active portion of the at least one sensor circuit and skin or other tissue of the user, and the substrate supporting and at least partially enclosing the transducer circuit and the electrical-signal sensing circuit, and conforming to the skin or the other tissue of the user and therein locating the conductive electrode layer sufficiently close to the skin or the other tissue with the layered portion being characterized in terms of thickness and flexibility for electrically sensing hemodynamic or pulse-wave events of an arterial pulse waveform manifesting primary peaks as pulse-waveform maxima and minima and manifesting one or more subtle features separated from the primary peaks and in between the pulse-waveform maxima and minima;

via the transducer circuit, converting the changes in capacitance into electrical signals, the changes in capacitance being responsive to at least one of pressure and electric field modulations attributable to the one or more features, via the electrical-signal sensing circuit, sensing the one or more features in response to the electrical signals from the transducer circuit, and using a communication circuit, within or outside the wearable apparatus, to respond to the electrical-signal sensing circuit by conveying data indicative of the one or more subtle features.

20. The method of claim 19, wherein the layered portion is characterized in terms of thickness and flexibility for the at least one sensor circuit to capture the hemodynamic or pulse-wave events via the electrical signals via at least one of a: pressure change in a range from 0.3 kilopascal to 1 kilopascal, and a capacitance change in a range defined as plus and minus 15 picofarads.

21. The method of claim 19, further including the communication circuit presenting or sending data indicative of the primary peaks as pulse-waveform maxima and minima and the one or more subtle features separated from the primary peaks and in between the pulse-waveform maxima and minima.

* * * * *